US011398312B2

(12) United States Patent
Todd et al.

(10) Patent No.: US 11,398,312 B2
(45) Date of Patent: Jul. 26, 2022

(54) PREVENTING THE FILL OF INEFFECTIVE OR UNDER-EFFECTIVE MEDICATIONS THROUGH INTEGRATION OF GENETIC EFFICACY TESTING RESULTS WITH LEGACY ELECTRONIC PATIENT RECORDS

(71) Applicant: Xact Laboratories, LLC, Twinsburg, OH (US)

(72) Inventors: Rob Todd, Doylestown, PA (US); Jerry Wrobel, Aurora, OH (US); John Pigott, Slyvania, OH (US)

(73) Assignee: Xact Laboratories, LLC, Twinsburg, OH (US)

( * ) Notice: Subject to any disclaimer, the term of this patent is extended or adjusted under 35 U.S.C. 154(b) by 78 days.

(21) Appl. No.: 16/945,198

(22) Filed: Jul. 31, 2020

(65) Prior Publication Data
US 2020/0365280 A1 Nov. 19, 2020

Related U.S. Application Data

(63) Continuation-in-part of application No. 16/848,504, filed on Apr. 14, 2020, which is a continuation-in-part
(Continued)

(51) Int. Cl.
*G16H 70/40* (2018.01)
*G16H 10/40* (2018.01)
(Continued)

(52) U.S. Cl.
CPC ....... *G16H 70/40* (2018.01); *G06F 16/90335* (2019.01); *G06Q 10/083* (2013.01);
(Continued)

(58) Field of Classification Search
USPC .......................................... 705/2–3
See application file for complete search history.

(56) References Cited

U.S. PATENT DOCUMENTS 6,315,720 B1  11/2001  Williams et al.
8,386,274 B1   2/2013  Pinsonneault
(Continued)

OTHER PUBLICATIONS

Jensen, Peter, et al., "Mining electronic health records: towards better research applications and clinical care", Translational Genetics, Nature Reviews: Genetics, vol. 13, Jun. 2012, pp. 395-405. (Year: 2012).*
(Continued)

*Primary Examiner* — Amber A Misiaszek
(74) *Attorney, Agent, or Firm* — Standley Law Group LLP; Adam J. Smith; Jeffrey S. Standley

(57) ABSTRACT

System and methods for preventing the coverage or fill of ineffective medications are provided. Genetic efficacy testing results are received at a pharmacy benefits manager ("PBM") system from a laboratory information system. Medications reported as ineffective in the testing results are flagged as an allergy in an electronic patient record. Requests for coverage of medications are received at the PBM system from a dispensing pharmacy system and electronic notifications are issued to the dispensing pharmacy system where the medication is flagged as an allergy at the PBM system to prevent the flagged medication from being filled.

20 Claims, 16 Drawing Sheets

Related U.S. Application Data of application No. 16/674,189, filed on Nov. 5, 2019, which is a continuation-in-part of application No. 16/441,597, filed on Jun. 14, 2019.

(60) Provisional application No. 62/773,424, filed on Nov. 30, 2018, provisional application No. 62/685,479, filed on Jun. 15, 2018.

(51) Int. Cl.

| | | |
|---|---|---|
| *G16H 50/70* | (2018.01) | |
| *G16H 40/20* | (2018.01) | |
| *G16H 50/20* | (2018.01) | |
| *G06Q 40/08* | (2012.01) | |
| *G16H 40/67* | (2018.01) | |
| *G06Q 10/10* | (2012.01) | |
| *G16H 70/60* | (2018.01) | |
| *G16H 70/20* | (2018.01) | |
| *G06Q 10/08* | (2012.01) | |
| *G06F 16/903* | (2019.01) | |
| *H04M 3/51* | (2006.01) | |
| *G16H 10/60* | (2018.01) | |
| *G06Q 30/04* | (2012.01) | |

(52) U.S. Cl.
CPC ............ *G06Q 10/10* (2013.01); *G06Q 40/08* (2013.01); *G16H 10/40* (2018.01); *G16H 10/60* (2018.01); *G16H 40/20* (2018.01); *G16H 40/67* (2018.01); *G16H 50/20* (2018.01); *G16H 50/70* (2018.01); *G16H 70/20* (2018.01); *G16H 70/60* (2018.01); *H04M 3/5158* (2013.01); *G06Q 30/04* (2013.01); *G06Q 2250/00* (2013.01)

(56) References Cited

U.S. PATENT DOCUMENTS

| | | | |
|---|---|---|---|
| 10,950,354 | B1 | 3/2021 | Belgoroski |
| 2002/0012921 | A1 | 1/2002 | Stanton, Jr. |
| 2002/0115073 | A1 | 8/2002 | Papadopoulos et al. |
| 2002/0147616 | A1 | 10/2002 | Pollard et al. |
| 2003/0040002 | A1 | 2/2003 | Ledley |
| 2005/0107672 | A1 | 5/2005 | Lipscher et al. |
| 2005/0149361 | A1 | 7/2005 | Saus et al. |
| 2006/0259325 | A1* | 11/2006 | Patterson ............... G06Q 40/02 705/2 |
| 2007/0178501 | A1 | 8/2007 | Rabinowitz et al. |
| 2008/0091464 | A1 | 4/2008 | Lipscher et al. |
| 2008/0131887 | A1 | 6/2008 | Stephan et al. |
| 2008/0162352 | A1 | 7/2008 | Gizewski |
| 2008/0228824 | A1* | 9/2008 | Kenedy ................ G16H 40/63 |
| 2009/0094059 | A1 | 4/2009 | Coleman et al. |
| 2009/0198519 | A1 | 8/2009 | McNamar |
| 2009/0240523 | A1* | 9/2009 | Friedlander ............ G16H 20/10 705/2 |
| 2010/0070455 | A1 | 3/2010 | Halperin et al. |
| 2010/0317006 | A1 | 12/2010 | Soykan et al. |
| 2012/0065999 | A1 | 3/2012 | Takatoku et al. |
| 2012/0185270 | A1 | 7/2012 | Scantland et al. |
| 2013/0096943 | A1 | 4/2013 | Carey et al. |
| 2013/0246079 | A1 | 9/2013 | Hoffman et al. |
| 2014/0303992 | A1 | 10/2014 | Scantland et al. |
| 2014/0316821 | A1 | 10/2014 | Sheffield et al. |
| 2014/0350954 | A1 | 11/2014 | Ellis et al. |
| 2014/0372141 | A1 | 12/2014 | Renner et al. |
| 2015/0058030 | A1 | 2/2015 | Scantland et al. |
| 2015/0058039 | A1 | 2/2015 | Shiloh |
| 2015/0170291 | A1 | 6/2015 | Renner et al. |
| 2015/0228030 | A1 | 8/2015 | Scantland et al. |
| 2016/0048652 | A1* | 2/2016 | Spivey .................. G16H 20/10 705/2 |
| 2016/0092652 | A1 | 3/2016 | Stewart et al. |
| 2016/0180063 | A1 | 6/2016 | Scantland et al. |
| 2016/0239636 | A1 | 8/2016 | O'Donnell et al. |
| 2017/0004282 | A1 | 1/2017 | Scantland et al. |
| 2017/0046491 | A1 | 2/2017 | Scantland et al. |
| 2017/0046492 | A1 | 2/2017 | Renner et al. |
| 2017/0213011 | A1 | 7/2017 | Hoffman et al. |
| 2017/0270246 | A1 | 9/2017 | Baskys |
| 2017/0308669 | A1 | 10/2017 | Apte et al. |
| 2018/0075220 | A1 | 3/2018 | Hill, Sr. et al. |
| 2018/0308569 | A1 | 10/2018 | Luellen |
| 2018/0330060 | A1 | 11/2018 | Biles et al. |
| 2019/0244688 | A1 | 8/2019 | Wilson et al. |

OTHER PUBLICATIONS

Clinisync, Clinisync Products and Services webpage, http://www.clinisync.org/, Jul. 18, 2018, 5 pages.

Althoff, Lisa, DNA Chip—Genetic Testing of the Future webpage, https://www.ndsu.edu/pubweb/~mcclean/plsc431/students99/althoff.html, Copyright 1999, Aug. 2, 2019, 5 pages.

Labx, DNA Sequencers Listings webpage, https://www.labx.com/dna-sequencers, Aug. 2, 2019, 3 pages.

Vecna, Veena Patient Solutions webpage, https://healthcare.vecna.com/, Jul. 18, 2019, 11 pages.

Translational Software, Making Sense of Pharmacogenomics Testing webpage, https://translationalsoftware.com/, Sep. 11, 2019, 14 pages.

Translational Software, Integrated Into Clinical Systems archived webpage, https://web.archive.org/web/20171217010330/https://translationalsoftware.com/, Oct. 17, 2017, 7 pages.

Translational Software, Insights Ready for Action archived webpage, https://web.archive.org/web/20180829020620/https://translationalsoftwarre.com/, Aug. 29, 2018, 9 pages.

Coriell Life Sciences, GeneDose—Medication Risk Management Tool archived webpage, https://web.archive.org/web/20170611205541/http://genedose.com/, Jun. 11, 2017, 8 pages.

Coriell Life Sciences, DNA-Driven Diagnostics To Guide Clinical Decision-Making webpage, https://www.coriell.com/genetic-interpretation-reporting/, Sep. 11, 2019, 9 pages.

Coriell Life Services, GeneDose Youtube Video, https://youtube.com/watch?v=tku6_9tADuw, Sep. 11, 2019.

Caraballo et al., Electronic Medical Record-Integrated Pharmacogenomics and Related Clinical Decision Support Concepts, Aug. 2017, Clinical Pharmacology & Therapeutics, vol. 102 No 2, pp. 254-264.

* cited by examiner

PREVENTING THE FILL OF INEFFECTIVE OR UNDER-EFFECTIVE MEDICATIONS THROUGH INTEGRATION OF GENETIC EFFICACY TESTING RESULTS WITH LEGACY ELECTRONIC PATIENT RECORDS

CROSS-REFERENCE TO RELATED APPLICATION

This application is a continuation-in-part of U.S. application Ser. No. 16/848,504 filed Apr. 14, 2020, which is a continuation-in-part of U.S. application Ser. No. 16/674,189 filed Nov. 5, 2019, which is a continuation-in-part of U.S. application Ser. No. 16/441,597 filed Jun. 14, 2019, which claims the benefit of U.S. Provisional Application Ser. No. 62/685,479 filed Jun. 15, 2018 and U.S. Provisional Application Ser. No. 62/773,424 filed Nov. 30, 2018, the disclosures of all of which are hereby incorporated by reference as if fully restated herein.

TECHNICAL FIELD

Exemplary embodiments relate generally to systems and methods for preventing the coverage or fill of ineffective medications based on genetic efficacy testing.

BACKGROUND AND SUMMARY OF THE INVENTION

A person visiting a doctor may present with one or more symptoms. Based on the symptoms presented, test results, or underlying conditions or diseases diagnosed, the person may be prescribed one or more medications or other treatment options by the healthcare provider as part of a treatment program. These treatments may be selected based on the historical effectiveness of such treatment options against the symptoms presented by the person and/or the underlying disease(s) or condition(s) diagnosed by the healthcare provider. Traditionally, the prescription of treatment options is, at least initially, based on historical effectiveness of certain medications against the diagnosed disease. Individual prescriptions may be altered through a trial and error process following the initial prescription. For example, alternative medications, dosages, or other treatments (e.g., surgery, herbal remedies, other therapies) may be prescribed where the prescription of a particular treatment option causes a side effect or allergic reaction in a patient and/or simply fails to achieve the desired outcome. Over prescription or dosing of treatments, particularly of medications, may cause side effects or other undesirable consequences. Under prescription or dosing of treatments, particularly of medications, may bring about ineffective results, side effects, or other undesirable consequences.

A person's genetic makeup often affects how the person responds to certain medical treatments, such as the administration of medications. For example, a person's genetic makeup may cause some medications or dosages to be wholly or partially ineffective. As used herein, the term ineffective may be understood to mean wholly or partially ineffective. As a further example, a person's genetic makeup may make surgery more or less desirable. Prescription of treatments to a person who has a genetic makeup that makes the treatment wholly ineffective may waste resources and unnecessarily expose the person to the risk of side effects. Similarly, prescription of treatments to a person who has a genetic makeup that makes the treatment partially ineffective may result in less than desirable therapeutic effects, require a larger dosage, or the like to be effective. In some cases, alternative medications, dosages, or other treatment options are available for use with the same, or similar, therapeutic effects.

For example, without limitation, a blood thinner may be known to reduce the risk of embolisms and may be prescribed to a person following stent placement. However, the patient's individual genetic makeup or physiology may alter the effectiveness of the prescribed blood thinner. For example, without limitation, the blood thinner may have a reduced effectiveness in persons carrying specific genetic markers. It would be desirable to substitute alternative medications or adjust the dosage of prescribed medications for persons having a genetic makeup which reduces the effectiveness of the prescribed medication. As a further example, again without limitation, the prescribed blood thinner may be wholly ineffective in persons carrying specific genetic markers. It would be desirable to substitute alternative medications, or find alternative treatment options, for persons having a genetic makeup which renders the prescribed medication ineffective. Therefore, what is needed is a system and method for determining the effectiveness of medications using genetics.

A persons' genetic makeup may determine the efficacy of other treatments beyond just medications. For example, without limitation, a persons' genomic makeup may be analyzed to determine the efficacy of various cancer treatment options. Such options may include various medications, such as chemotherapy, but may also include surgery, radiation, active surveillance, and other treatment approaches.

Current systems, such as electronic medical record systems ("EMRs"), are often unable to accept genomic information in a meaningful way and/or lack a dedicated space for such genetic information. For example, EMRs often do not have a designated page, portal, display, or the like for genomic testing results to be displayed. Therefore, what is needed is a system and method for integrating genetic efficacy information with existing systems.

Being a cutting-edge field, genomics testing is often not part of a healthcare provider's routine care plan. A healthcare provider may not even be aware that certain genomic testing is available that can determine the efficacy of various treatment options, such as medications. Therefore, what is needed is a system and method for determining eligibility for genetic efficacy testing.

These disclosures provide systems and methods for determining the effectiveness of treatment options, such as medications, using genetic data. A user's visit information may be reviewed to identify applicable tests. For example, such tests may indicate the presence or non-presence of genetic markers which may indicate a genetic makeup for a patient that may have a bearing on the effectiveness of one or more treatments prescribed, and/or likely to be prescribed, to the user.

The disclosed systems and methods may be applied to any number of genomic efficacy tests. For example, without limitation, genomic testing may be ordered to determine the patient's likelihood of developing certain cancers and/or the efficacy of various treatment options for different types of cancer.

The disclosed systems and methods may streamline the ordering and eligibility process. The system may be configured to determine whether identified tests fit certain billing parameters. For example, the system may be configured to determine whether the identified tests are covered by the user's insurance. If the test for one or more markers does not fit the billing parameters, then the next genetic marker(s) may be considered. If the test does fit the billing parameters then the option to order testing may be presented to the healthcare provider. If selected, the appropriate marker(s) may be added to a testing device and the genetic testing may be performed. In exemplary embodiments, diagnostic and treatment codes may be entered by the healthcare provider into their system. A determination may be made as to whether certain genetic efficacy testing meets various insurance eligibility criteria, such as but not limited to, medically necessary criteria. If so, the respective genomic tests may be automatically added to an order list. In this way, all available testing for which the patient is eligible may be automatically added to an ordering list, thereby increasing the availability of potentially relevant information to the healthcare provider. The order list may be subsequently displayed to the healthcare provider for confirmation, though in other exemplary embodiments the order list may be automatically processed.

To perform the testing, genetic material may be removed from the user. A testing device may be created to test for the specific genetic marker(s) ordered. The genetic material may be sequenced using the testing device and the presence or non-presence of the tested genetic markers may be determined. The results may be analyzed and ineffective treatment options, such as but not limited to medications, may be identified. In exemplary embodiments, for each treatment prescribed or likely to be prescribed, the presence or non-presence of one or more genetic markers may be analyzed and compared against the treatments known to be effective or ineffective in the presence of the given marker. Effective treatments and/or dosages may be identified. Alternatively, or additionally, ineffective treatments and/or dosages may be identified. For those treatments and/or dosages determined to be ineffective, alternative medications, dosages, and/or treatment options may be suggested.

Integration into existing EMRs, electronic health records ("EHR"), and other healthcare provider systems may be performed by designating ineffective medications or other treatment options as an allergy in the user's file. This may provide a pathway for integration with existing EMRs, EHRs, and other healthcare provider systems. Advantageously, in exemplary embodiments, this solution may configure the EMR, EHR, or other healthcare provider system to generate an alert upon selection of a medication or other treatment options designated by the testing results to be ineffective. In this way, the disclosed systems and methods may be integrated within the framework of existing systems to prevent the costs and complexities of redesigning the existing systems.

Regardless, the testing results may be returned to the healthcare provider's system. For example, treatment of a particular disease may normally first begin with medication. However, if the person has a genetic makeup which would make such medication ineffective, a surgical option may instead be suggested.

The results may be returned to the healthcare provider in the form of an interface for display on an electronic display. The results may be displayed in a fashion which provides the clinical consequences of prescribing the treatment. The interface may further provide indications of particular conditions and generate alerts when particular conditions are met. For example, without limitation, executable software instructions may be provided which configure the electronic display to display an interface comprising an explanation of the results, alerts, abnormal ranges, ineffective treatments, potential interactions as understood in view of the analyzed genetic information, and other clinical information. This information may be transmitted with the results in a single file.

In exemplary embodiments, these results and alerts may be integrated into the healthcare providers' EHR by way of a single file, though multiple files may be utilized. In exemplary embodiments, the results of the ordered tests, including but not limited to the ineffective treatment options, may be transmitted to a healthcare information exchange ("HIE"). The HIE may subsequently distribute the results to a number of linked healthcare provided systems and/or make such data available for access. This information may be further transmitted to any number of healthcare provider facilities, such as but not limited to hospitals, by way of one or more HIEs. For example, information may be transmitted to all healthcare providers treating the user. The results may also be stored for use by, and selective transmission to, future healthcare providers. In this way, the disclosed systems and methods may integrate with existing healthcare provider systems, such as EHRs and HIEs to facilitate the ordering of such genomic efficacy tests and integrate the results into the framework of existing systems. Furthermore, integration with a number of healthcare provider systems may be accomplished by integration with one or more HIEs.

Genetics testing, such as but not limited to genetics-based medication efficacy testing, is a burgeoning field. Not all payors support genetic testing, and those that do often have specific rules regarding which types of testing are covered and which are not. Conventionally, to determine if the genetic testing will be covered, a representative of a healthcare provider's office contacts a patient to obtain certain information, which is then passed to the payor for prior authorization of the proposed genetic tests. This work is taxing on patients and healthcare provider office staff. It also results in duplicate information being generated for prior authorization purposes and laboratory ordering purposes. Furthermore, the patient sometimes owes a copay, and the healthcare provider's office is further burdened with collecting payment from the insured, paying the laboratory for testing, and collecting amounts owed from the patient. This results in complex management and transfer of funds.

Laboratories typically do not have sufficient information or resources to perform the prior authorization request. For example, without limitation, the laboratory may not have access to the patient's health history such as but not limited to disease diagnosis and active medications, which are sometimes required to determine if the ordered genetic testing is medically necessary. Therefore, what is needed is a system and method for laboratory-based authorization of genetic testing.

Systems and methods for automatically providing laboratory-based authorization of genetic testing are provided. An order may be generated at a healthcare provider's EHR or other system. The order may be initiated by a healthcare provider and may be based on suggested orders from the laboratory. A specimen for testing may be sent from the healthcare provider to the laboratory. The order information may be sent electronically from the healthcare provider's office system or EHR to a laboratory information system ("LIS") associated with a laboratory. The LIS may automatically parse information from the order. The LIS may be in electronic communication with the EHR and electronically retrieve certain patient health information.

The LIS may use the parsed order data and/or retrieved health information to automatically generate an electronic prior authorization requests which may be electronically transmitted to the appropriate party for communication and/or approval. The appropriate party may include, for example without limitation, the payor, the call center, a prior authorization provider, some combination thereof, or the like. The appropriate party may return a reference ID and a patient responsibility amount. The patient responsibility may represent an amount owned by the patient such as, but not limited to, a copayment, deductible, coinsurance, some combination thereof, or the like. If the patient responsibility exceeds a predetermined threshold, a call center notice may be automatically generated and transmitted to the laboratory and/or a call center. The call center and/or laboratory may contact the patient to obtain a virtual billing consent to proceed. The virtual billing consent may be consistent with a signed informed billing consent presented to the patient in the office at the time of the testing is ordered and/or the genetic material is gathered. If consent is denied, or if a predetermined number of attempts are made to contact the patient without success, the specimen may be destroyed and the order terminated. If consent is received, payment may be collected, such as in real time when obtaining the virtual billing consent, and the testing may be allowed to proceed. If the patient responsibility is below the predetermined threshold, testing may proceed. Testing results may be generated and transmitted to the healthcare provider. In exemplary embodiments, the prior authorization and virtual billing consent process may be completed while the specimen is in transit to the laboratory.

While all types of genetic testing are contemplated, certain advantages may be realized in particular for genetics-based medication efficacy testing. For such testing, the LIS may query the EHR to obtain a list of active medications. Alternatively, or additionally, the LIS may query the EHR to obtain a list of diagnoses and use that list to generate a list of medications likely to be prescribed to the patient. The efficacy of one or more of the listed medications may be tested. This same list of medications and/or diagnoses may be used in making prior authorization decisions, for example without limitation, to determine which tests are medically necessary. Thus, in at least one embodiment, the invention improves the processing capabilities and speed by eliminating duplicate information and reducing burdens on electronic storage.

Electronic funds management is another technological challenge. Under conventional approaches, the healthcare provider acts as a collector and payor for the laboratory, whose is the driver of fees for the testing. By utilizing the laboratory to directly obtain prior authorization and collects funds, the complexity and challenges of electronic funds management and transfer are significantly reduced or eliminated. This may reduce the number of potential security intrusion standpoints, the number of parties needing to secure financial information, the number of funds transfers, and the like. It also may place the collection risk on the laboratory instead of the healthcare provider.

The disclosed systems and methods may reduce the number of human interactions required, thereby improving data processing times and/or accuracy. The electronic automation may result in faster, more accurate, and more consistent data processing. The disclosed systems and methods may reduce the amount of paper transferred, data faxed, telephone calls made, voicemails recorded, and the like, all of which may serve as additional points to data intrusion. In this way, the communication pipeline may be streamlined to reduce the number of access points and improve data security. The disclosed systems and methods may reduce the need for resources at the healthcare provider office reducing business costs and complexity.

It takes time to receive data, specimens, perform genetic efficacy testing, generate reports, notify healthcare providers, and then notify patients of results. In some cases, this delay in time may be long enough that the patient may have already filled their prescription and/or begun using it. This results in wasted prescriptions, driving up costs in the healthcare system. Therefore, what is needed is a system for preventing the coverage or fill of ineffective prescribed medications based on genetic efficacy testing.

Systems and methods for preventing the coverage or fill of ineffective prescribed medications based on genetic efficacy testing are provided. Patent data received at the LIS may include prescription information. A notification regarding ordered prescriptions flagged as ineffective may be sent to a pharmacy benefits provider ("PBM") which interfaces with the pharmacy. The interfacing with a PBM is an effective way to reach a large number of patients as it is common for a PBM to manage pharmacy benefits for a larger population of individuals. The notification may indicate that one or more medications have been determined to be ineffective based on the person's genetic makeup. Upon attempt to receive insurance coverage for such ineffective medications, the PBM may notify the pharmacy that coverage is denied and/or to not fill one or more such prescriptions, thereby preventing the patient from ever receiving the medication and reducing costs. The notification may indicate that one or more prescribed medications have been determined to be effective based on the person's genetic makeup. Upon attempt to receive insurance coverage for such effective medications, the PBM may notify the pharmacy to proceed with filling one or more such prescriptions, thereby reducing costs by ensuring only effective medications are filled. In other exemplary embodiments, a lack of notification after a period of time may be treated as an indication that such prescribed medications are considered effective. The PBM may flag ineffective medications as an allergy in the electronic file associated with patient. This may permit integration into existing systems and flag future attempts to prescribe and/or approve coverage for the medication.

Where one or more prescriptions are indicated as being ineffective, the LIS may be configured to supply alternative medications in the notification which are effective based on the patient's genetic makeup. In such cases, the PBM may notify the pharmacy of such alternatives which may be presented to the patient for approval and/or filled. The notification may comprise the full report transmitted to the healthcare provider's office, or may be a simplified version. In other exemplary embodiments, the notification may be sent directly to a pharmacy.

The systems and methods shown and/or described herein may permit for vertical integration of laboratory testing results. For example, without limitation, such testing results may be vertically integrated across payor systems, PBM systems, laboratory systems, EHR systems, HIE systems, pharmacy systems, some combination thereof, or the like.

Further features and advantages of the devices and systems disclosed herein, as well as the structure and operation of various aspects of the present disclosure, are described in detail below with reference to the accompanying figures.

BRIEF DESCRIPTION OF THE DRAWINGS

In addition to the features mentioned above, other aspects of the present invention will be readily apparent from the following descriptions of the drawings and exemplary embodiments, wherein like reference numerals across the several views refer to identical or equivalent features, and wherein.

DETAILED DESCRIPTION OF EXEMPLARY EMBODIMENT(S)

Various embodiments of the present invention will now be described in detail with reference to the accompanying drawings. In the following description, specific details such as detailed configuration and components are merely provided to assist the overall understanding of these embodiments of the present invention. Therefore, it should be apparent to those skilled in the art that various changes and modifications of the embodiments described herein can be made without departing from the scope and spirit of the present invention. In addition, descriptions of well-known functions and constructions are omitted for clarity and conciseness.

Figure 1A:
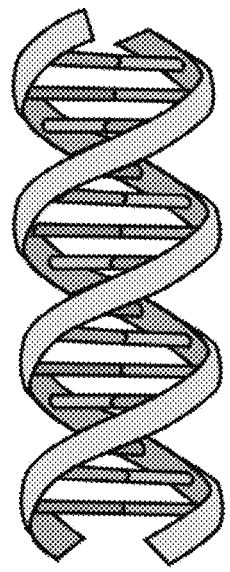
FIG. 1A is a simplified illustration of a DNA helix.

FIG. 1A is a simplified illustration of a DNA helix 4. DNA, or deoxyribonucleic acid, is a double-helix shaped chain of nucleotides that carry the genetic instructions used in the growth, development, functioning, and reproduction of all known living organisms. There are four major types of nucleobases in any nucleotide of a DNA sequence, which are generally coded as A, T, C, and G for adenine, thymine, cytosine, and guanine, respectively. Each individual human is believed to have a unique DNA structure that defines the persons' genetic makeup.

Figure 1B:
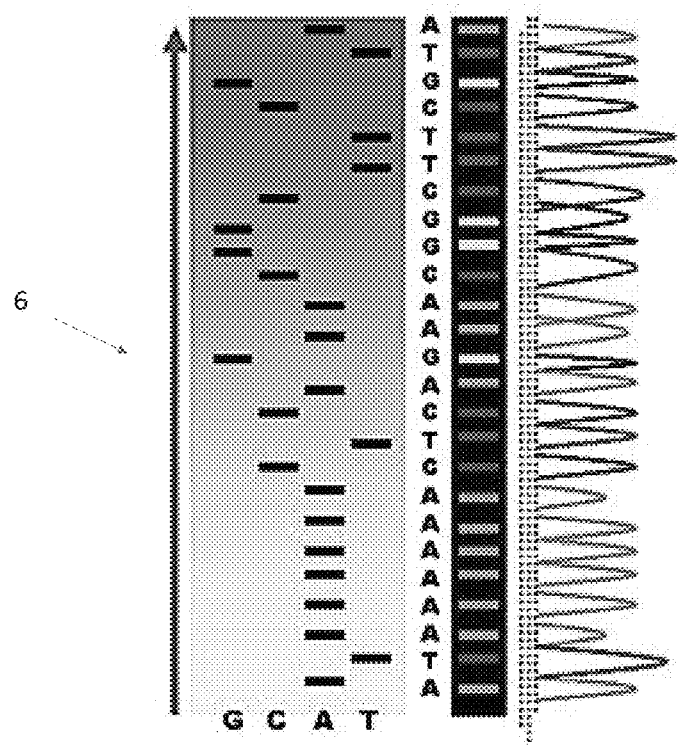
FIG. 1B is a simplified illustration of a DNA sequencing test result.

FIG. 1B is a simplified illustration of a DNA sequencing test result 6. Upon sequencing of the DNA 4, the presence or non-presence of particular nucleobases (A, T, C, or G) may be detected. The presence and non-presence or order of such nucleobases can be used to determine the presence or non-presence of certain genetic markers. The genetic markers may indicate the existence or non-existence of certain genetic traits for the person.

Figure 2:
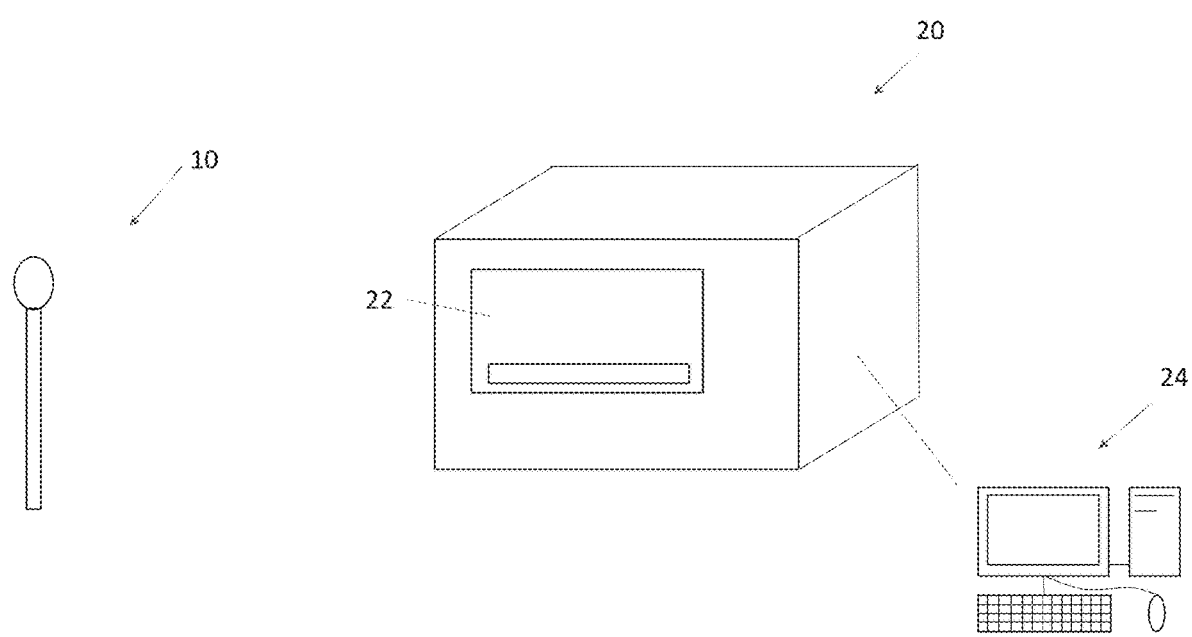
FIG. 2 is a simplified perspective view of an exemplary genetic material gathering device and an exemplary sequencing device.

FIG. 2 is a simplified perspective view of an exemplary genetic material gathering device 10 and an exemplary genetic sequencing device 20. The genetic material gathering device 10 may comprise a swab, syringe, vial, strip, or the like. For example, without limitation, the genetic material gathering device 10 may comprise a swab configured to be used on the inside of the user's cheek to gather saliva and/or skin cells. In other examples, without limitation, the genetic material gathering device 10 may comprise a syringe configured to gather blood, a vial configured to store blood, hair, skin samples, or the like, some combination thereof, or the like. Any type of genetic material gathering device 10 for gathering any type of genetic material is contemplated.

The genetic sequencing device 20 may comprise any kind of device configured to sequence genetic material. In exemplary embodiments, the genetic sequencing device 20 may comprise a loading area 22 and a control panel 24. The loading area 22 may be configured to accept one or more testing devices 30. The control panel 24 may be integrally formed with the genetic sequencing device 20 or may be a separate electronic device in communication with the genetic sequencing device 20. The control panel 24 may be configured to accept user input comprising instructions for carrying out various genetic tests on the testing device 30. The control panel 24 may be configured to display the results of such testing. Such instructions may, alternatively or additionally, be accepted from a remote device, which may comprise the control panel 24 or another device. Testing results may be transmitted to one or more remote devices and/or systems as further described herein.

Figure 3:
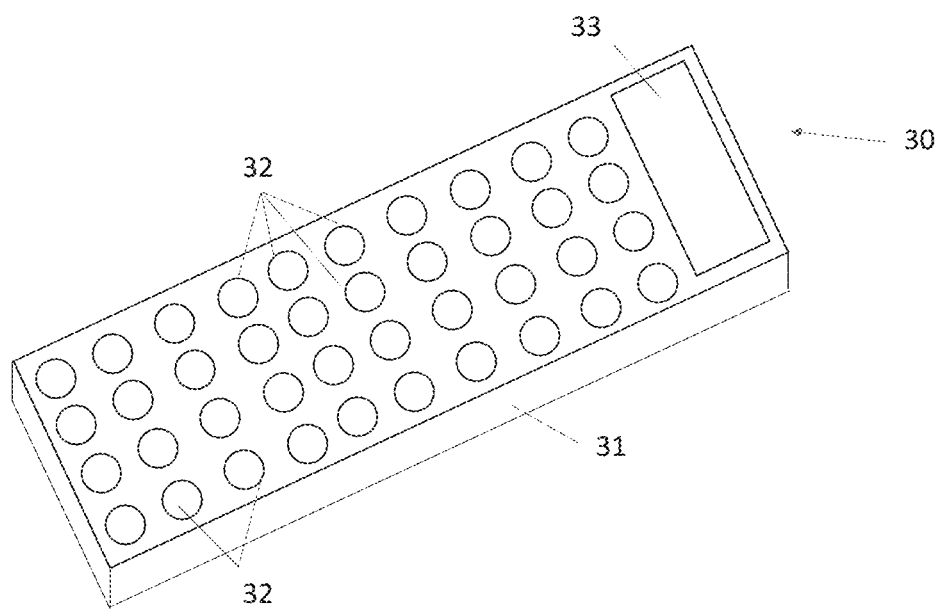
FIG. 3 is a simplified perspective view of an exemplary genetic testing device for use with the sequencing device of FIG. 2.

FIG. 3 is a simplified perspective view of an exemplary genetic testing device 30 for use with the sequencing device 20. In exemplary embodiments, the testing device 30 may comprise a chip 31 comprised of a number of wells 32, though any type of testing device 30 is contemplated. Each of said wells 32 may be configured to test for a particular genetic marker. The testing device 30 may be configured to accommodate any number of wells 32. In exemplary embodiments, certain wells 32 may be added or removed from the testing device 30 in order to test for the presence or non-presence of various genetic markers. For example, without limitation, wells 32 may be added to the chip 31 to test for particular genetic traits and wells 32 may be removed from the chip 31 if a particular genetic trait is not being tested for. In still other exemplary embodiments, the wells 32 being used may be placed in an unblocked position such that genetic material may enter the well 32. Similarly, the wells 32 not being used may be placed in a blocked position such that genetic material may not enter the wells 32. Modifications to the testing device 30 may be performed manually or automatically based on the instructions for testing received. For example, without limitation, the testing device 30 may be constructed or modified by one or more robots. The testing device 30 may further comprise one or more areas 33 to affix labels, markers, or the like, and may comprise, for example without limitation, unique identifiers, barcodes, QR codes, some combination thereof, or the like.

Figure 4A:
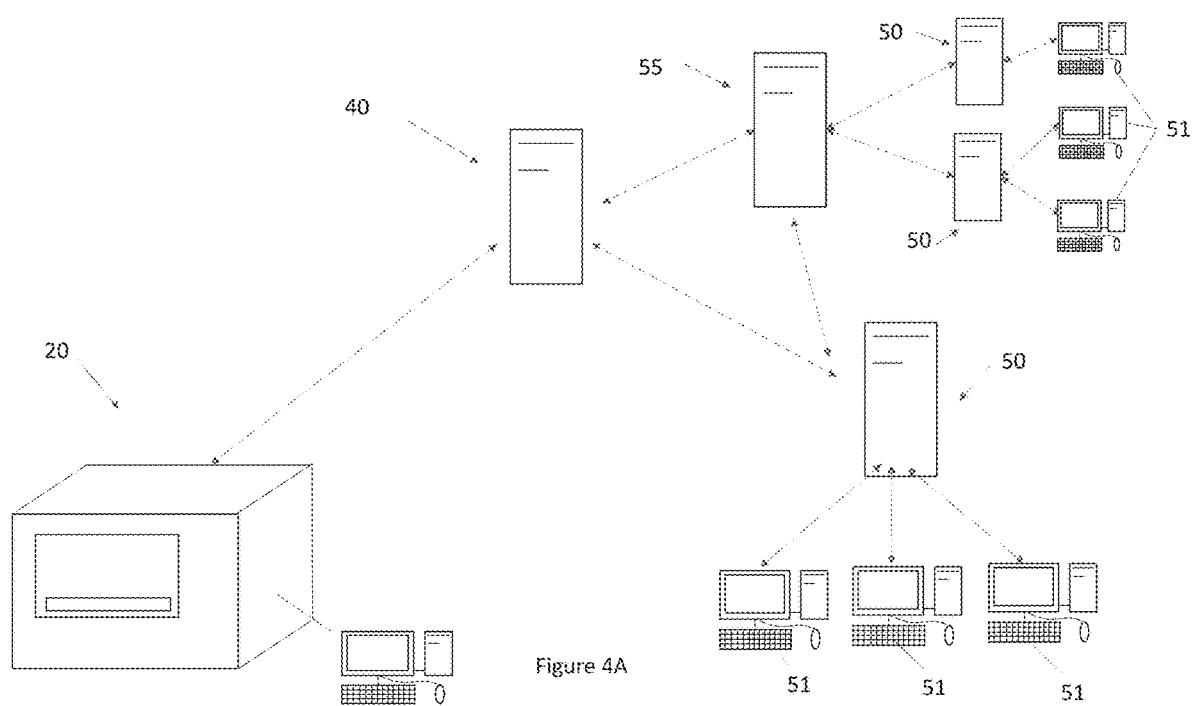
FIG. 4A is a simplified plan view of an exemplary system for providing genetic efficacy testing results, including the sequencing device of FIG. 2.

FIG. 4A is a simplified plan view of an exemplary system for providing genetic efficacy testing results. The genetic sequencing device 20 may be in electronic communication with a laboratory system 40. The laboratory system 40 may receive testing instructions which are communicated to one or more genetic sequencing devices 20. The laboratory system 40 may also be configured to receive the results of any performed tests from the one or more genetic sequencing devices 20. More than one laboratory system 40 may be provided, each of which may be in communication with one or more genetic sequencing devices 20. In exemplary embodiments, the laboratory system 40 may be a laboratory facing system, such as but not limited to a laboratory information system ("LIS"). The laboratory system 40 may be in electronic communication with one or more healthcare provider systems 50. Each of the healthcare provider systems 50 may comprise patient information, a list of ordered tests, and test results, among other data. The healthcare provider systems 50 may communicate instructions for genetic efficacy tests to be performed to the laboratory system 40. The results of such ordered genetic efficacy tests may be transmitted from the laboratory system 40 to one or more of the healthcare provider systems 50. In exemplary embodiments, the healthcare provider systems 50 may be healthcare provider facing system such as, but not limited to, an electronic medical record ("EMR") system, electronic health record ("EHR"), some combination thereof, or the like. Although some embodiments are discussed with respect to a certain number of genetic sequencing devices 20, laboratory systems 40, and healthcare provider systems 50, any number of such components are contemplated.

The sequencing device 20, the laboratory system 40, and the healthcare provider system 50 may be located in the same facility, or may be remote from one another. The electronic communication may be by way of a wired or a wireless connection. The electronic communication may further be made by way of one or more network interface devices and one or more communication networks located at each of the sequencing device 20, the laboratory system 40, and the healthcare provider system 50. The communications networks utilized may include, but are not limited to, the internet, intranet, cellular network, or the like. In exemplary embodiments, communications between the genetic sequencing device 20, the laboratory system 40, and/or the healthcare provider system 50 may be made secured and encrypted. Alternatively, or additionally, such communications may be made in a standardized format such as, but not limited to, a HL7 format. In exemplary embodiments, the genetic efficacy test results may be pulled from the laboratory system 40 such as, but not limited, to by the use of scanning and archiving software. The testing results may be automatically integrated into the healthcare provider system 50. Such integration may be performed by way of a flat file, though any method of integration is contemplated. For example, without limitation, the testing results may be automatically integrated into the EHR utilized by the healthcare provider, preferably as further described herein.

Alternatively, or in addition, the test results may be made available to the healthcare provider by way of an internet-based portal accessed through the healthcare provider system 50 or any number of personal electronic devices 51 in electronic communication with, or constituting, the healthcare provider system 50. In particular, a hyperlink to the portal may be provided to the healthcare provider system 50 such that it is stored as a quick link access, though such is not required. As yet another example, without limitation, the testing results may be provided to the healthcare provider by way of email to the healthcare provider system 50. In other embodiments, the testing results may be made available to the healthcare provider by way of an application installed on the various personal electronic devices 51.

The test results stored on the laboratory system 40 may be secured such that a particular healthcare provider can only access the results for users associated with the particular healthcare provider. For example, without limitation, permission may be set such that login credentials associated with a given healthcare provider may be permit access to test results for particular users associated with that healthcare provider. The laboratory system 40 may be configured to periodically download testing results from the genetic sequencing device 20. Similarly, the laboratory system 40 may be configured to periodically download testing results to the healthcare providers system 50. Alternatively, or in addition, certain results may be downloaded on demand. Access to the testing data, including but not limited to testing results, may be protected by way of security protocols, such as, but not limited to, authentication, biometric scanning, single sign-on, barcode scanning protocols, some combination thereof, or the like. The automation and reduction in human interaction provided by the disclosed systems and method may reduce the number of potential intrusion points and improve data security.

Each of the sequencing devices 20, the laboratory systems 40, and the healthcare provider systems 50 may comprise one or more electronic components. Such electronic components may include, but are not limited to, processors, electronic storage devices, user input devices, displays, and the like. Each of the sequencing devices 20, the laboratory systems 40, and the healthcare provider systems 50 may comprise software instructions configured to perform the steps and functions described herein.

Figure 4B:
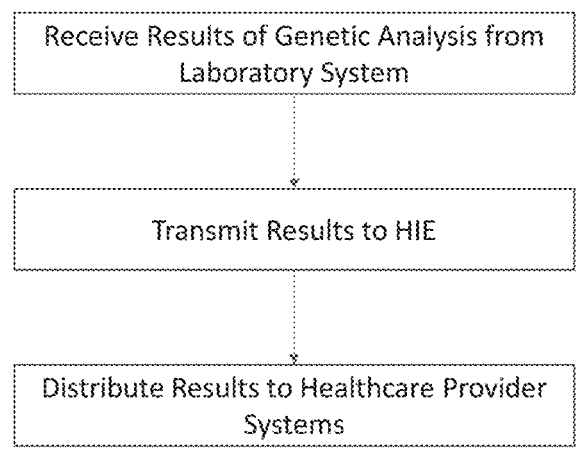
FIG. 4B is a flow chart with exemplary logic for distributing the test results.

FIG. 4B is a flow chart with exemplary logic for distributing the genetic efficacy test results. In exemplary embodiments, test results may be received from the laboratory system 40 at a health care information exchange ("HIE") 55. The HIE 55 may be in electronic communication with a number of healthcare provider systems 50. Each of the healthcare provider systems 50 may be in electronic communication with one or more personal electronic devices 51. The HIE 55 may be configured to automatically distribute the test results to each healthcare provider system 50 associated with a healthcare provider known to be treating the patient. In other exemplary embodiments, the HIE 55 may make the testing results available for integration into any of the linked healthcare provider systems 50.

In exemplary embodiments, the necessary integration of the laboratory system 40 and/or genetic efficacy test results may be performed only with respect to a single HIE 55 to permit integration with a number of linked healthcare provider systems 50. This also may permit information for specific data, such as but not limited to unusual cases, to be shared across healthcare providers who may be geographically remote from one another and/or associated with different practices such that the most relevant information may be made available to healthcare decision makers. For example, without limitation, the efficacy data for a patient seen with a relatively rare genetic makeup in Connecticut may be sent to a doctor in Oregon who has a different patient with a similar genetic makeup.

Figure 5A:
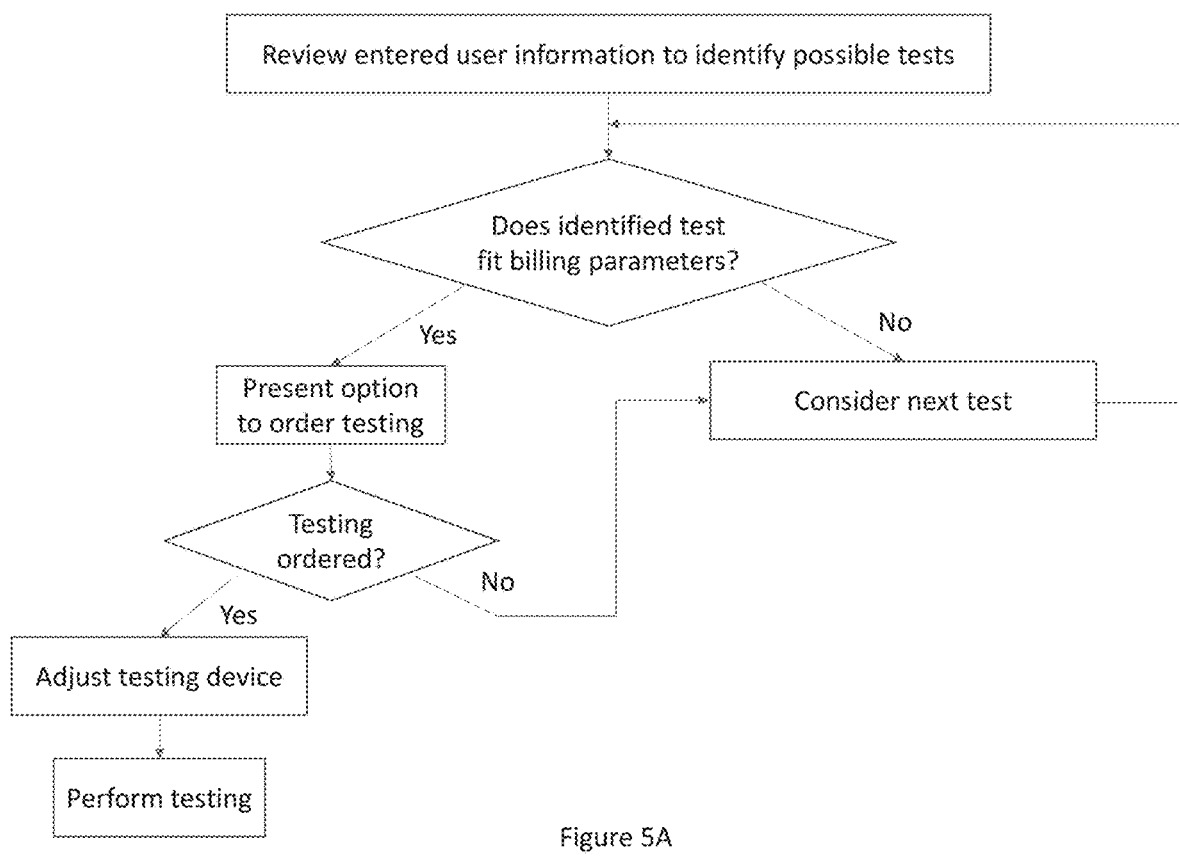
FIG. 5A is a flow chart illustrating exemplary logic for identifying, ordering, and performing tests.

FIG. 5A is a flow chart illustrating exemplary logic for identifying, ordering, and performing genetic efficacy tests. A user may visit one or more healthcare providers and present with a variety of symptoms. As the healthcare provider evaluates the user, including by taking a medical history, evaluating symptoms, and performing tests, the healthcare provider may enter information about the user into the healthcare providers' system 50. Already existing information about the user may already be present on the healthcare providers' system 50, though such is not required. Such information already existing or entered by the healthcare provider might include, for example but without limitation, identification information, demographic information, insurance information, medical history, known allergies, family history, some combination thereof, and the like. In exemplary embodiments, the healthcare provider system 50 comprises an EMR and/or an EHR. The entered information by the healthcare provider at a given visit may include, for example but without limitation, treatment actions taken or prescribed, symptoms presented, diagnosed diseases or conditions, tests ordered, testing results, some combination thereof, and the like. In exemplary embodiments, at least the treatment actions taken or prescribed and the diseases or conditions diagnosed may be entered and/or converted into codes, such as but not limited to, ICD codes, though any type, protocol, or format of coding is contemplated.

In exemplary embodiments, certain information about the patient may be retrieved by the laboratory system 40 from the healthcare provider system 50 such as, but not limited, to by the use of scanning and archiving software. The laboratory system 40 may review the entered information and identify conditions diagnosed, or likely to be diagnosed, treatments prescribed, or likely to be prescribed, to the patient. The treatments likely to be prescribed, such as but not limited to medications, may be determined by comparing the entered information with standard treatment procedures. Such standard treatment procedures may be stored at the laboratory system 40, or at one or more separate databases, and may be sourced from public and private data sources. For example, without limitation, if a stent placement is ordered for the patient, the laboratory system 40 may determine that post-operative blood thinners are likely to be prescribed. The conditions likely to be diagnosed may be determined by comparing the entered information, such as symptoms and test results, with diseases associated with such information. Such disease information may be stored on the laboratory system 40, or one or more separate database, and may be sourced from public and private data sources. For example, without limitation, if chest pain is reported, a likely condition of heart disease may be determined.

The laboratory system 40 may identify one or more genetic markers that may have a bearing on the effectiveness of prescribed, or likely to be prescribed, treatments. The laboratory system 40 may determine whether testing for the identified genetic markers fits one or more billing parameters. For example, without limitation, the laboratory system 40 may determine whether such testing would be considered medically necessary under Medicare regulations and/or guidelines. An exemplary listing of medically necessary codes is provided in tables 1-2 below. The provided tables are merely exemplary and are not intended to be limiting.

TABLE 1

Cardiovascular Diagnostic Codes

| Code | Description |
| --- | --- |
| 120.0 | Unstable angina |
| 120.1 | Angina pectoris with documented spasm |
| 120.8 | Other forms of angina pectoris |
| 120.9 | Angina pectoris, unspecified |
| 121.09 | ST elevation (STEMI) myocardial infarction involving other coronary artery of anterior wall |

TABLE 1-continued

Cardiovascular Diagnostic Codes

| Code | Description |
| --- | --- |
| 121.11 | ST elevation (STEMI) myocardial infarction involving right coronary artery |
| 121.19 | ST elevation (STEMI) myocardial infarction involving other coronary artery |
| 121.29 | ST elevation (STEMI) myocardial infarction involving other sites |
| 121.3 | ST elevation (STEMI) myocardial infarction of unspecified site |
| 121.4 | Non-ST elevation (NSTEMI) myocardial infarction |
| 124.0 | Acute coronary thrombosis not resulting in myocardial infarction |
| 124.1 | Dressler's syndrome |
| 124.8 | Other forms of acute ischemic heart disease |
| 124.9 | Acute ischemic heart disease, unspecified |
| 125.110 | Atherosclerotic heart disease of native coronary artery with unstable angina pectoris |
| 125.700 | Atherosclerosis of coronary artery bypass graft(s), unspecified, with unstable angina pectoris |
| 125.710 | Atherosclerosis of autologous vein coronary artery bypass graft(s) with unstable angina |
| 125.720 | Atherosclerosis of autologous artery coronary artery bypass graft(s) with unstable angina pectoris |
| 125.730 | Atherosclerosis of nonautologous biological coronary artery bypass graft(s) with unstable angina pectoris |
| 125.750 | Atherosclerosis of native coronary artery of transplanted heart with unstable angina |
| 125.760 | Atherosclerosis of bypass graft of coronary artery of transplanted heart with unstable angina |
| 125.790 | Atherosclerosis of other coronary artery bypass graft(s) with unstable angina pectoris |

TABLE 2

Psychiatric and Pain Management Diagnostic Codes

| Code | Description |
| --- | --- |
| F31.30 | Bipolar disorder, current episode depressed, mild or moderate severity, unspecified |
| F31.31 | Bipolar disorder, current episode depressed, mild |
| F31.32 | Bipolar disorder, current episode depressed, moderate |
| F31.4 | Bipolar disorder, current episode depressed, severe, without psychotic features |
| F31.5 | Bipolar disorder, current episode depressed, severe, with psychotic features |
| F31.60 | Bipolar disorder, current episode mixed, unspecified |
| F31.61 | Bipolar disorder, current episode mixed, mild |
| F31.62 | Bipolar disorder, current episode mixed, moderate |
| F31.63 | Bipolar disorder, current episode mixed, severe, without psychotic features |
| F31.64 | Bipolar disorder, current episode mixed, severe, with psychotic features |
| F31.75 | Bipolar disorder, in partial remission, most recent episode depressed |
| F31.76 | Bipolar disorder, in full remission, most recent episode depressed |
| F31.77 | Bipolar disorder, in partial remission, most recent episode mixed |
| F31.78 | Bipolar disorder, in full remission, most recent episode mixed |
| F31.9 | Bipolar disorder, unspecified |
| F32.9 | Major depressive disorder, single episode, unspecified |
| F33.0 | Major depressive disorder, recurrent, mild |
| F33.1 | Major depressive disorder, recurrent, moderate |
| F33.2 | Major depressive disorder, recurrent severe without psychotic features |
| F33.3 | Major depressive disorder, recurrent, severe with psychotic symptoms |
| F33.40 | Major depressive disorder, recurrent, in remission, unspecified |
| F33.41 | Major depressive disorder, recurrent, in partial remission |
| F33.42 | Major depressive disorder, recurrent, in full remission |
| F33.9 | Major depressive disorder, recurrent, unspecified |
| G10 | Huntington's disease |

In exemplary embodiments, if any of the diagnostic codes provided by the healthcare provider system 50 fit the provided billing parameters, then the genetic testing may automatically be included in the plan of treatment for that patient.

Alternatively, or additionally, the laboratory system 40 may be configured to gather and review insurance information for coverage eligibility for particular types of testing. The laboratory system 40 may be configured to determine whether such testing would be wholly or partially covered by the user's insurance. This may be performed by reviewing the billing codes against those codes covered by the user's insurance. This may alternatively or additionally be performed by interfacing with the user's insurance provider. Regardless, in such embodiments, the billing parameters may comprise the testing known or likely to be approved. These billing parameters may be predetermined and preprogrammed and may be selected based on the user's insurance coverage.

Alternatively, or in addition, the laboratory system 40 may be configured to generate one or more forms for gathering and authorizing payment information for desired testing. For example, without limitation, the laboratory system 40, or a separate payment system, may be configured to store and authorize credit card transactions to pay for the ordered testing. This option may be provided to, for example without limitation, users who do not have insurance or elect not to bill insurance for such testing. This option may also be provided to cover any co-payment, patient responsible portions, some combination thereof, or the like. In such cases, the billing parameters may be any testing elected by the user. The generated forms may be electronic in nature and may be generated by the laboratory system 40 for display to the user and return to the laboratory system 40 for storage, though such is not required.

If the test fits the billing parameters, an option to order testing may be presented to the healthcare provider at the healthcare provider system 50. If not, then the test for the next genetic marker may be considered. Alternatively, or additionally, if the test fits the billing parameters, it may be automatically added to a list of ordered tests. The presentment of options to order testing may be controlled by the laboratory system 40, though such is not required.

If the healthcare provider orders the test, or the test is automatically added, the appropriate wells 32 may be added to, or removed from, the testing device 30 to test for the specified genetic markers. Alternatively, or in addition, the appropriate wells 32 may be blocked or unblocked on the testing device 30 to test for the specified genetic markers. Once all identified tests are considered, instructions for assembly of the testing device 30 may be transmitted and the testing may be performed.

In exemplary embodiments, user information may be gathered, or presented, using one or more secured means. For example, without limitation, information may be gathered and entered into the personal electronic devices 51 running a secured browser application. The personal electronic devices 51 may comprise remote shunt down capabilities and a variety of security protocols, such as but not limited to, authentication, biometric scanning, single sign-on, barcode scanning protocols, some combination thereof, or the like may be utilized.

Other information gathered from the user may include scanned copies of insurance card and photo ID. Forms such as digital consent forms, educational information, questionnaires, and medical necessity forms may be digitally filled out, stored, and/or transmitted. The laboratory system 40 and/or the healthcare provider system 50 may be configured to generate a QR code, barcode, label, or other identifier for attachment to the genetic material gathering device 10, the genetic testing device, paperwork, some combination thereof, or the like. Scanning of the QR code, barcode, label, or another identifier may automatically retrieve the associated user information.

Figure 5B:
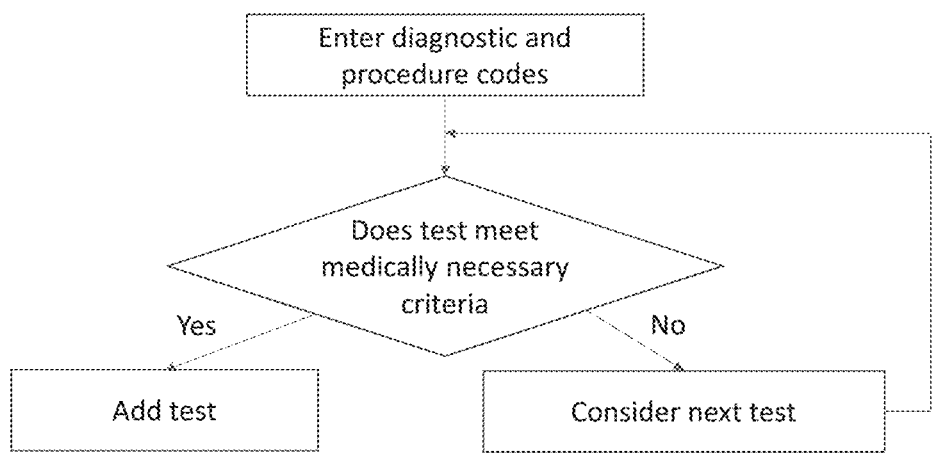
FIG. 5B is a flow chart illustrating other exemplary logic for identifying and ordering tests.

FIG. 5B is a flow chart illustrating other exemplary logic for identifying and ordering tests. Diagnostic and/or procedure codes may be entered by the healthcare provider. Preferably, such diagnostic and/or procedures codes are entered at the respective personal electronic device 51 for the respective healthcare provider system 50. The diagnostic and/or procedure codes may conform to International Classification of Diseases ("ICD"), though any type, standard, protocol, etc. of coding is contemplated. If the diagnostic and/or procedure codes meet medically necessary criteria for a given genetic efficacy test, for example without limitation, then the test may be automatically added to a list of ordered tests to be transmitted to the laboratory system 40. If the diagnostic and/or procedure codes fail to meet medically necessary criteria, for example without limitation, then the next test may be considered until all possible tests are exhausted.

Once all tests are considered, the list of order tests may be transmitted to the laboratory system 40. The diagnostic and/or procedure codes may be utilized to determine which genetic efficacy tests are relevant. In other exemplary embodiments, a list of particular genetic tests may be considered for each patient. The medically necessary criteria may be under Medicare and/or Medicaid guidelines, though any protocol, standard, or the like is contemplated. Other criteria are contemplated in addition to, or as an alternative to, the medically necessary criteria.

In this way, eligible test results may be automatically added to an order. Being a cutting-edge field, genomic efficacy testing is sometimes unknown or under considered by healthcare providers. The disclosed systems and methods not only permit the determination of insurance eligibility for such testing, but may automatically add such eligible tests to help ensure that a patient receives the highest quality of care and maximizes the information available to healthcare providers.

Figure 6A:
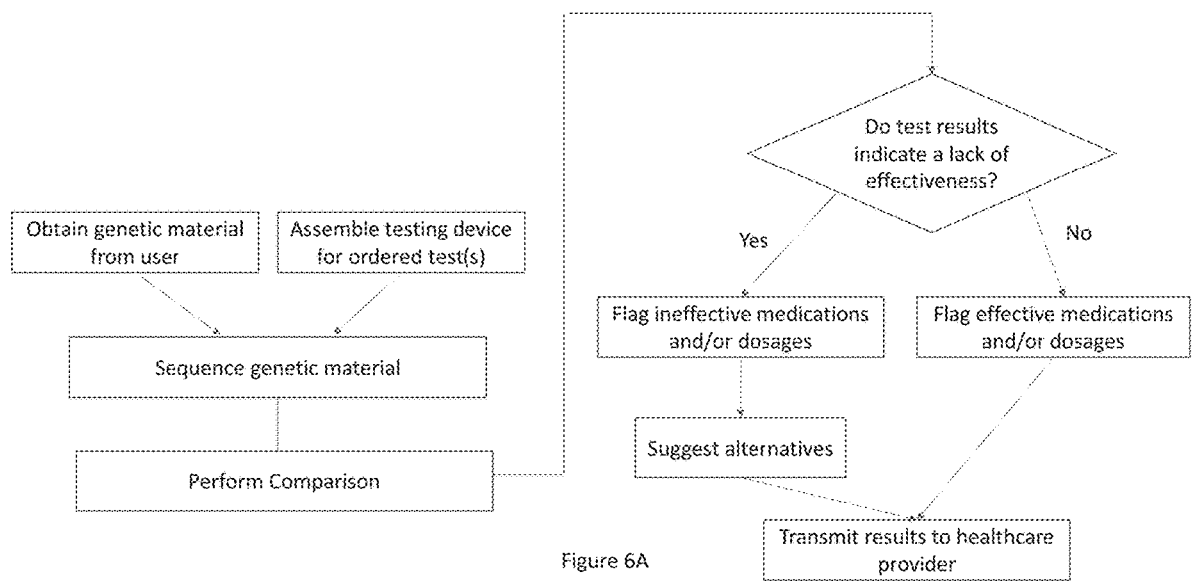
FIG. 6A is a flow chart illustrating exemplary logic for performing genetic efficacy testing and analyzing results.

FIG. 6A is a flow chart illustrating exemplary logic for performing genetic efficacy testing and analyzing results. Genetic material from the user may be gathered by way of the genetic material gathering device 10. A genetic testing device 30 comprising wells 32 for the ordered testing may be assembled. Such assembly may be performed manually or automatically. Such assembly may be performed concurrently, before, or after obtaining the genetic material. The genetic material may then be sequenced using the genetic sequencing device 20.

The testing may determine the presence or non-presence of the genetic markers for which the testing is performed. The results of such testing may be transmitted to the laboratory system 40. The results may be compared against information stored in the laboratory system 40, or elsewhere, regarding the effectiveness of given treatment options, such as but not limited to medications, in persons having or not having particular genetic markers. In particular, the results may be compared for each of the treatments prescribed to the user, or likely to be prescribed to the user. Similarly, the results may be compared against information stored in the laboratory system 40, or elsewhere, regarding the need for particular dosages or treatments in persons having or not having particular genetic markers. In particular, the results may be compared for each of the treatments and/or dosages prescribed to the user, or likely to be prescribed to the user.

Such information may be gathered from one or more public or private sources such as, but not limited to, the human genome project. In exemplary embodiments, the laboratory system 40, the healthcare provider system 50, and/or another system may be configured to prompt the healthcare provider to perform a follow-up telephone call regarding the test results a period of time after electronically transmitting the results to the patient.

The laboratory system 40 may be configured to flag ineffective treatments and/or dosages. Likewise, the laboratory system 40 may be configured to flag effective treatments and/or dosages. In exemplary embodiments, the results may be color coded. For example, without limitation, red color coding may indicate an ineffective treatment and/or dosage. A yellow color coding may indicate the need to adjust the treatment and/or dosage or monitor use of the therapy. A green color coding may indicate that the treatment and/or dosage is acceptable. Other colors and types of coding are contemplated.

The results of the testing may be transmitted to the healthcare provider system 50. The laboratory system 40 may be configured to automatically suggest alternative medications, or dosages, or treatment options for those treatments flagged to be ineffective or requiring adjustments. Furthermore, the healthcare provider system 50 may be updated to reflect the ineffectiveness of the treatments and/or dosages. For example, without limitation, ineffective treatments may be flagged or otherwise coded as an allergy in the user's file. More specifically, ineffective treatments may be identified in the message to the healthcare provider. For example, without limitation, this information may be added to the HL7 electronic results, such as but not limited to the PathX HL6 electronic communication, that are received with the test results and embedded into any .pdf type files generated from the HL7 file.

Alternatively, or in addition, additional parties may be notified of treatments and/or dosages determined to be ineffective. Such parties may include, but are not limited to, pharmacists, project managers, healthcare practice administrators, insurance providers, users, other healthcare providers, other approved persons, and the like. The results of the testing may be transmitted to each parties' respective system 50.

One or more healthcare information exchanges ("HIEs") may be utilized to provide information between various systems 50 and individuals. For example, without limitation, the results of the testing may automatically be shared with the healthcare provider system 50 for each healthcare provider treating the user. Each healthcare provider treating the user may automatically be granted access to the results of the testing, such as by way of the respective healthcare provider's personal electronic device 51. In exemplary embodiments, the HIE 55 may provide two-way communication such that information may be transmitted to and from the laboratory system 40.

Figure 6B:
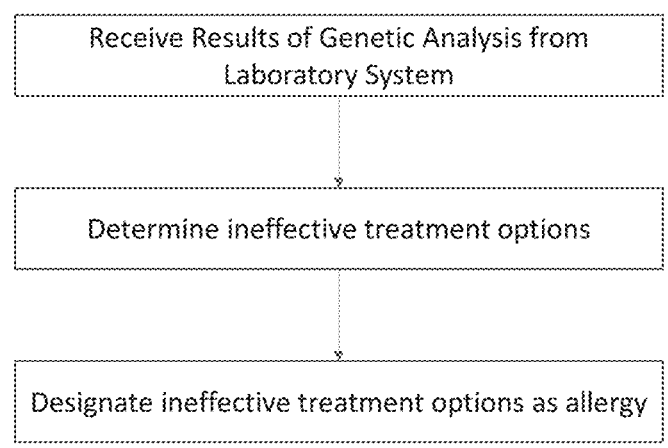
FIG. 6B is a flow chart illustrating exemplary logic for integrating genetic efficacy test results within existing systems.

FIG. 6B is a flow chart illustrating exemplary logic for integrating genetic efficacy test results within existing healthcare provider systems 50. Existing healthcare providers system 50, such as but not limited to EHRs, may not have a dedicated space for the integration of genomic testing results. Redesigning existing systems to provide such a dedicated space would be time consuming and expensive. As such, in exemplary embodiments, after receiving the genetic efficacy testing results and determining which treatment options are ineffective and/or have a reduced efficacy, such treatment options may be designated as an allergy in the user's file. Many, if not all, existing healthcare provider systems 50 have a designated space for the notation of allergies. As such, this provides a pathway for integration of genomic efficacy testing results into the patient's electronic file. Helpfully, in many cases, the healthcare provider system 50 is configured to raise an alert or otherwise provide some kind of notification upon prescription of such treatments flagged as an allergy. In this way, for example without limitation, ineffective medications and/or dosages may be alerted to the healthcare provider when ordering at the healthcare provider system 50.

Figure 7:
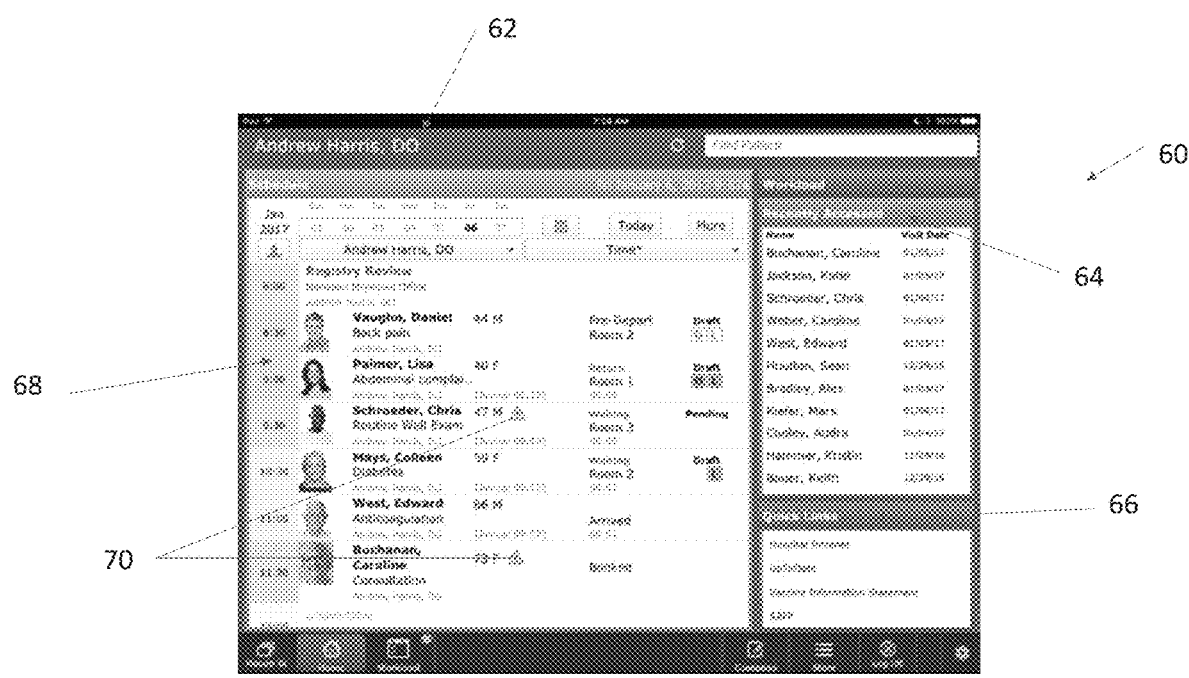
FIG. 7 is an exemplary healthcare provider interface.

FIG. 7 is an exemplary healthcare provider interface 60. The healthcare provider interface 60 may be displayed on one or more personal electronic devices 51 in electronic communication with the healthcare provider system 50. The personal electronic devices 51 may include computers, smartphones, tablets, some combination thereof, or the like. The interface 60 may provide results for one or more patients. The interface 60 may alternatively, or in addition, provide the results for multiple medications for a one or more patients. In exemplary embodiments, the results may be presented with the clinical consequences of prescribing each of the therapies. For example, without limitation, the interface 60 may inform the healthcare provider of whether the prescribed therapy is likely to be effective, partially effective, wholly ineffective, or the like. The healthcare provider interface 60 may be updated for each individual healthcare provider user 62. The healthcare provider's recently accessed files may be identified 64. A quick links section 66 may include a link to the portal for test ordering and results. A schedule 68 may include one or more indicators 70 which patient(s) have possible warnings associated with their test results. For example, without limitation, the results may be color coded. Such warnings may be provided as a result of coding the ineffective treatment options as an allergy in the user's file.

In other exemplary embodiments, indicators 70 may be presented in the form of alerts. Such alerts may include pop-ups, warning signals, electronic messages, some combination thereof, or the like. Such indicators 70 may be generated upon the receipt of results which indicate that the healthcare provider has prescribed a treatment, such as but not limited to a drug, to a patient known to be a non-responder to such treatments, the presence of abnormal result or range, the prescription of a treatment known to cause an allergic effect in the patient, or the prescription of a treatment which may potentially cause an interaction with a drug previously prescribed to the patient, or with a disease the patient is diagnosed with as understood in view of the analyzed genetic information. Other clinical information may be transmitted and displayed on the interface 60 such as, without limitation, an explanation of the results.

Figure 8:
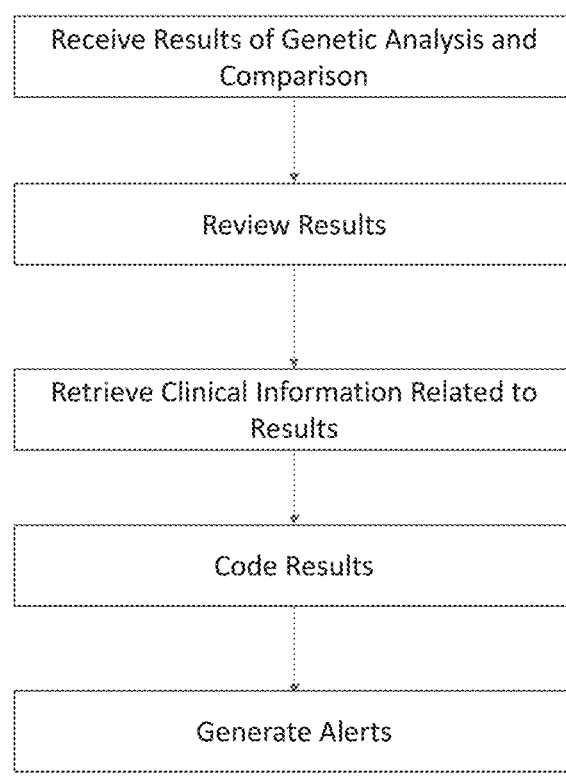
FIG. 8 is a simplified block diagram illustrating exemplary logic for analyzing genetic efficacy test results and generating alerts.

FIG. 8 is a simplified block diagram illustrating exemplary logic for analyzing genetic efficacy test results and generating alerts. Once the results of the genetic analysis are received, they may be reviewed. The review may include a comparison against information known about the patient, for example, by analyzing the patient's medical records as stored at one or more of the healthcare provider systems 50. For example, without limitation, the results may be reviewed to determine if the healthcare provider has prescribed, or is likely to prescribe, a treatment, such as but not limited to a drug, to a patient known to be a non-responder to such treatments, if the results include an abnormal result or range, if the healthcare provider has prescribed a treatment known to cause an allergic effect in the patient, and/or if the healthcare provider has prescribed a treatment which may potentially cause an interaction in view of the analyzed genetic information. The clinical information required to support this analysis may be retrieved from one or more databases, such as but not limited to, the healthcare provider system 50 or a database comprising various known medical information such as known drug interactions based on genetic makeup, normal results or ranges for various medical tests, and the like. The results of this review may be used to code the results displayed at the interface 60 or generate alerts as appropriate.

The comparison, analysis, and the like described herein may be performed at the laboratory system 40 or at the healthcare provider system 50. It is contemplated that any type of clinical information may be transmitted for display at the interface 60. The genetic information and test results may be stored at the laboratory system 40, the healthcare provider system 50, and/or another system to also be used against future prescribed treatments. In this way, the testing results may stay with the patient such that they can be referred to in the future as a person's genetic makeup generally remains unchanged throughout their life.

The clinical consequence of prescription, in exemplary embodiments, may be added to the electronic results and embedded into a single file for transmission to the healthcare provider system 50, though multiple files may be utilized. This may remove the need for use of multiple file types between the laboratory system 40, the healthcare provider system 50, and the electronic displays or individual systems 51. This may alternatively, or in addition, remove the need for multiple file types to be transmitted to one of the aforementioned systems. For example, one file with the results and another file with any alerts or other clinical information, though such an embodiment is contemplated. In exemplary embodiments, the results and all other related clinical information may be transmitted in a single standardized file, such an HL7 type file, though any file type is contemplated. This may permit the report to be integrated into any EHR system. In other exemplary embodiments, such clinical consequences may be transmitted by designating the particular treatment options likely to be ineffective or undereffective as an allergy. In exemplary embodiments, the genetic information and/or test results may be temporarily stored at the laboratory system 40 and/or another electronic storage device such that the data may be reformatted or otherwise modified as required to integrate with the HIE 55 and/or the various healthcare provider systems 50.

The coding and alerts described herein may be individualized based on the preferences of each user or entity. For example, when communicating results to a first healthcare provider system 50, alerts may be generated only when certain predetermined conditions are met. Likewise, when communicating results to a second healthcare provider system 50 alerts may be generated only when other predetermined conditions are met which may be the same or different from (with some overlap, complete overlap, or no overlap) with the predetermined conditions used to generate alerts for communications to the first healthcare provider system 50. Similarly, preferences may be altered for each personal electronic device 51.

In exemplary embodiments, the results may be transmitted along with educational information regarding the genetic testing results, a space for progress notes, and order information. In exemplary embodiments, the laboratory system 40, the healthcare provider system 50, or another system, may automatically schedule a follow up telephone encounter for approximately 1 week after the results are transmitted or the order is placed for testing.

Figure 9:
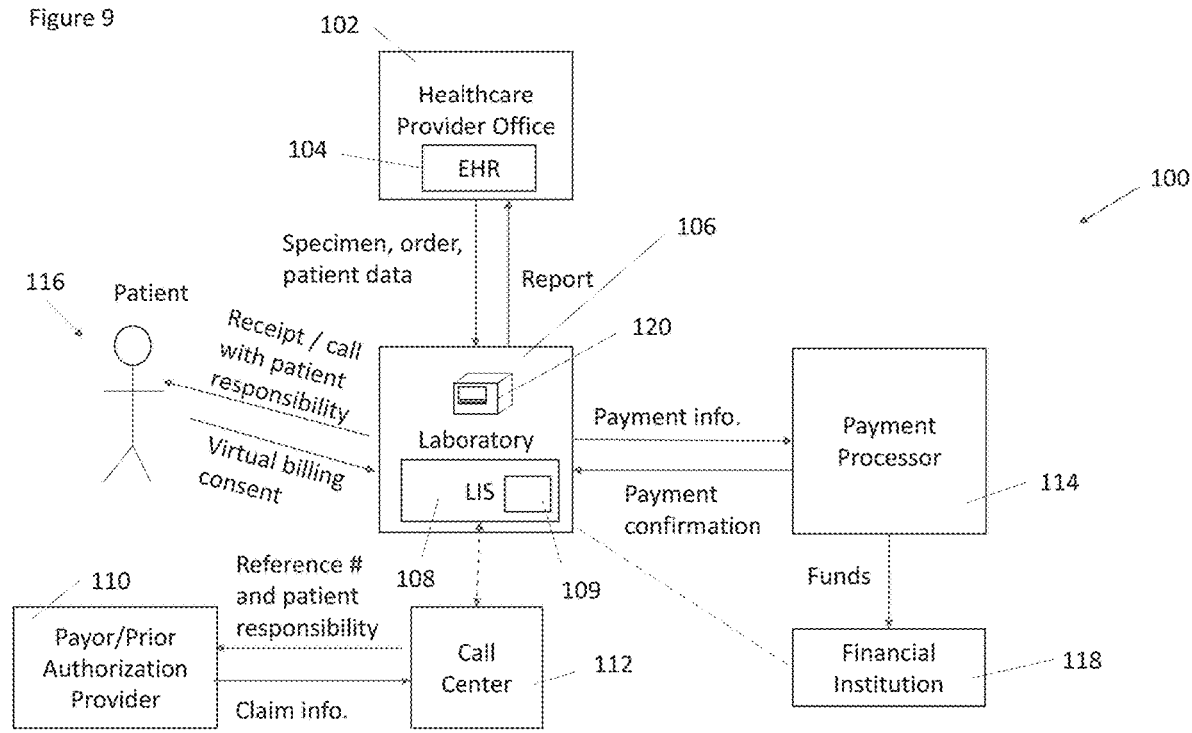
FIG. 9 is an exemplary laboratory-based prior authorization system in accordance with the present invention.
Figure 10:
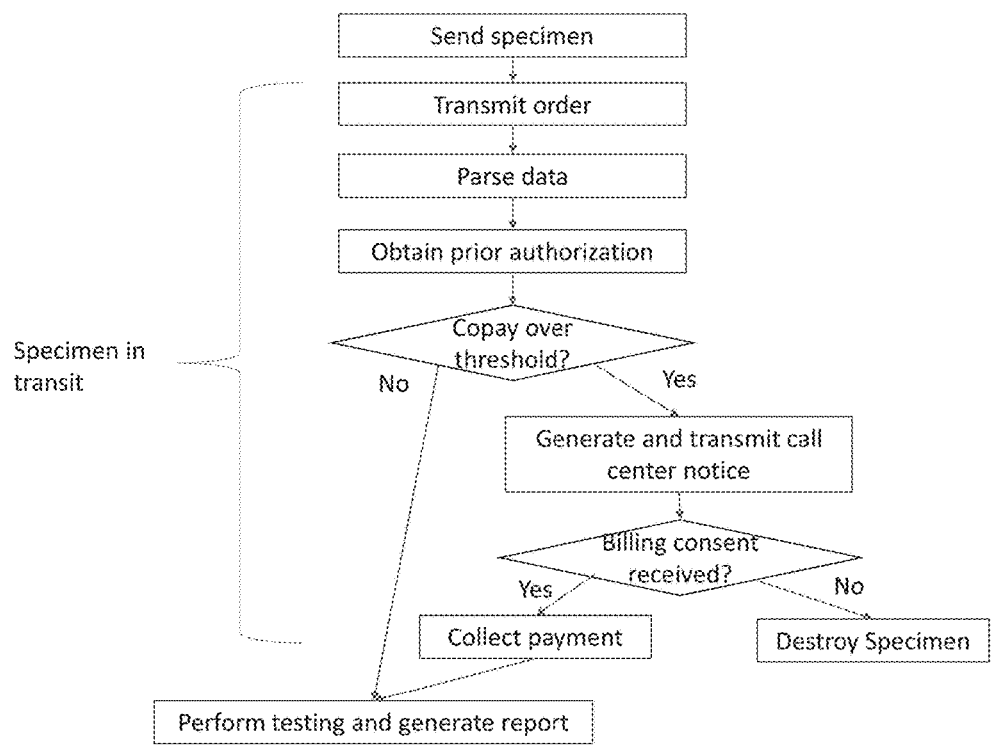
FIG. 10 in a flowchart with exemplary logic for operating the system of FIG. 9.

FIG. 9 illustrates an exemplary laboratory based prior authorization system 100. FIG. 10 illustrates exemplary logic for operating the system 100. The system 100 may comprise one or more healthcare provider office systems 102. The healthcare provider office system 102 may comprise one or more EHR systems 104, though the use of EMRs is also contemplated. While illustrated as part of the healthcare provider system 102, the EHR 104 may be separate from, and in electronic communication with, the healthcare provider office system 102. The healthcare provider office system 102 may comprise, alternatively or additionally, one or more telephones, fax machines, personal electronic devices, displays, databases, servers, some combination thereof, or the like. The EHR system 104 may comprise health information regarding one or more patients. The EHR system 104 may comprise medications, diagnoses, insurance information, identifying information, medical history information, billing information, contact information, some combination thereof, or the like.

The healthcare provider office system 102 may be in electronic communication with a laboratory system 106. The laboratory system 106 may comprise a Laboratory Information System ("LIS") 108. The laboratory system 106 may comprise, alternatively or additionally, one or more telephones, fax machines, personal electronic devices, displays, databases, servers, some combination thereof, or the like. The laboratory system 106 may comprise one or more genetic sequencing devices 120. The genetic sequencing devices 120 may each be in electronic communication with the LIS 108. The genetic sequencing devices 120 may each be the same or similar to genetic sequencing devices 20 shown and described with respect to FIG. 2. The genetic sequencing devices 120 may each comprise a controller, which may include the same or similar to the control panel 24 shown and described with respect to FIG. 2, though such is not required.

Order information may be transmitted from the healthcare provider office system 102 to the laboratory system 106. The order may be transmitted in electronic form. In exemplary embodiments, the order may comprise an HL7 order. The order may be transmitted from the EHR 104 to the LIS 108, though such is not required. A specimen for the order may be transmitted from the healthcare provider office system 102 to the laboratory system 106. The specimen may comprise the genetic material gathering device 10, which may comprise genetic material for testing. In other exemplary embodiments, optical recognition software may be utilized to recognize and input order information.

It is notable that any number of healthcare provider offices 102 may be utilized and be in electronic communication with the laboratory system 106. Each healthcare provider office system 102 may have its own EHR system 104 or may share EHR systems 104 with other healthcare provider office systems 102.

The order may be transmitted electronically. The laboratory system 106 may receive the order and automatically parse the data to generate one or more prior authorization requests. In exemplary embodiments, the order may be transmitted from the EHR 104 and/or received at the LIS 108, which may be configured to perform the electronic parsing and prior authorization request generation. In exemplary embodiments, the electronic parsing and prior authorization request generation may be performed by an automated pre-approval request engine 109. The parsed data may comprise, for example without limitation, identification information, demographic information, insurance information, order information, diagnosis information, current procedural terminology (CPT) information, active medications for the patient, some combination thereof, or the like. At least some of this information may, alternatively or additionally, be obtained by electronic query of the EHR system 104. Retrieval from the EHR system 104 may ensure that the most updated information is being utilized. Updated information may be automatically utilized without the need to send a redundant update to the LIS 108 as such updated information may be automatically retrieved and integrated.

In exemplary embodiments, the active medication and/or diagnosis information may be obtained from the EHR 104 and may facilitate the ability for the payor or prior authorization provider 110 to determine the medical necessity of the ordered testing. The prior authorization request may comprise the data parsed from the incoming genetic tests order and/or information retrieved from the EHR 104. The LIS 108 may be configured to retrieve such data and generate a prior authorization request formatted in the fashion desired by the payor or prior authorization provider 110. In this way, the laboratory system 106 may be positioned to automatically obtain prior authorization without additional involvement of the healthcare provider office system 102. This may prevent the duplication of data at both the healthcare provider office system 102 and the laboratory system 106. In exemplary embodiments, such information may be retrieved, parsed, formatted, and transmitted by the automated pre-approval request engine 109, though such is not required.

In exemplary embodiments, the LIS 108 may be configured to generate and submit a prior authorization request before an order is submitted. For example, without limitation, the LIS 108 may be prompted by the healthcare provider office system 102 to review a specific patient file for eligible genetic tests. As another example, without limitation, the LIS 108 may be configured to review new entries made at the EHR 104 for eligible genetic tests. In such cases, the same or substantially the same, systems and methods may be utilized to obtain prior authorization and generate a list of eligible tests in the form of a proposed order which is transmitted to the healthcare provider office system 102 for approval. The EHR 104 may be configured to display the proposed order for affirmation by the healthcare provider. In other exemplary embodiments, the proposed order may be automatically placed.

The parsed information may be automatically transformed into one or more prior authorization requests. The prior authorization request(s) may be transmitted from the laboratory system 106 to the payor or prior authorization provider 110. The payor or prior authorization provider 110 may process the prior authorization request(s) and return a reference identifier and/or patient responsibility amount to the laboratory system 106. For example, without limitation, the patient responsibility may comprise a monetary amount due, a copayment, a deductible, coinsurance, a denial of coverage, an approval of coverage, a percentage of costs due, a negotiated price, an amount covered, some combination thereof, or the like. The reference identifier may comprise a number, code, or other unique identifier.

The patient responsibility may be determined by applying one or more policy rules. The policy rules may be stored at a database. The policy rules may comprise eligibility determinations based on the ordered tests, diagnostic codes, treatment codes, some combination thereof, or the like. The policy rules, additionally or alternatively, may comprise medically necessary criteria. The policy rules may comprise patient responsibility rules, such as not but not limited to, co-pays, coinsurance, deductibles, negotiated rates, some combination thereof, or the like. The policy rules may be specific to various policies provided by the payor. The payor or prior authorization provider 110 may be configured to retrieve the policy rules based on the patient information and/or insurance information received and apply the policy rules to the ordered tests to determine eligibility and patient responsibility.

Where the patient responsibility is below a predetermined threshold, the LIS 108 may be configured to transmit instructions to the genetic sequencing device 120 to initiate the ordered testing. Upon completion, the results may be returned from the genetic sequencing device 120 to the LIS 108. The LIS 108 may be configured to transmit the results, such as but not limited to, in notification, instruction, and/or report form, to the EHR system 104. For example, without limitation, the predetermined threshold may be $50 USD. Any amount may be utilized for the predetermined threshold. Where the patient responsibility is above the predetermined threshold, a call center notice may be automatically generated by the laboratory system 106 and transmitted to a call center system 112. The call center notice may be transmitted from the automated pre-approval request engine 109, in exemplary embodiments. In exemplary embodiments, the automated pre-approval request engine 109 and/or the LIS 108 may be in direct electronic communication with the payor or prior authorization provider 110.

The call center notice may comprise information from the parsed data and/or returned from the payor or prior authorization provider 110. Such information may be communicated to the automated pre-approval request engine 109, in exemplary embodiments. In exemplary embodiments, an electronic notification may be automatically generated with call center notices for all claims received from the payor or prior authorization provider 110 in a given period of time. The electronic notification may be transmitted to the call center system 112. The call center system 112 may be provided at the laboratory 106 or may be remote therefrom. For example, without limitation, an encrypted email may be automatically generated periodically with attached call center notices for all claims processed by the payor or prior authorization provider 110 in a period of time, such as but not limited to the prior 1-24 hours. Any time period is contemplated such as, but not limited to, 4 hours, 12 hours, 24 hours, some combination thereof, or the like. In this way, one may simply check to see that the electronic notifications are being periodically transmitted to verify that the system is functioning properly. This may result in consistent, faster data processing.

The call center system 112 may be configured to contact the patient 116 and inform the patient 116 of the patient responsibility required to proceed. The call center system 112 may comprise one or more automatic dialers, text message generators, email generators, some combination thereof, or the like. For example, without limitation, the call center system 112 may be configured to automatically extract patient contact information, such as but not limited to, phone numbers, email addresses, some combination thereof, or the like, and automatically generate messages and/or dial, text, email, some combination thereof, or the like the patient to obtain the patient's consent to proceed.

Payment information may be collected and/or processed by a payment processing system 114. The payment processing system 114 may be internal to the call center system 112 or external. The payment information collected and/or processed may comprise credit card information, debit card information, electronic checks, wire information, bank account information, some combination thereof, or the like.

The payment processor 114 may be configured to process the payment information received. The payment processing system 114 may return confirmation of payment. The funds may be electronically transferred to a financial institution 118, such as but not limited to a bank, associated with the laboratory system 106. In this way, the number of parties having access to sensitive financial information is reduced. This may prevent the need to transmit funds between multiple institutions. This may reduce the number of access points to sensitive financial information, thereby increasing data security.

Where the patient 116 elects not to proceed with the ordered testing, notification regarding the same may be transmitted from the LIS 108 to the EHR 104. Such notification may additionally be transmitted from the call center system 112 to the LIS 108. In exemplary embodiments, where a predetermined number of contact attempts are made from the call center system 112 to the patient 116, and no reply is received, the patient 116 may be deemed to have not consented. For example, without limitation, the predetermined number of attempts may be three attempts. The call center system 112 may be configured to automatically track the number of attempted contacts. For example, without limitation, an automated dialer at the call center system 112 may be configured to extract and automatically dial the user three times, if no call is picked up, the user may be deemed to have not consented. Upon receipt of notification of denial of consent (whether through explicit denial, lack of ability to contact patient, or otherwise) the specimen may be destroyed. For example, without limitation, the call center system 112 may be configured to generate an electronic notification regarding the denial which is transmitted to the LIS 108, which in turn generates instructions to destroy the specimen.

Upon receipt of notification of consent and/or payment, the LIS 108 may generate instructions to the genetic sequencing device 120 to begin testing the specimen. For example, without limitation, the call center system 112 may be configured to generate an electronic notification regarding the consent and/or payment which is transmitted to the LIS 108, which in turn generates instructions to proceed with the ordered testing. The specimen may be analyzed and results regarding the same may be generated and transmitted to the LIS 108. The LIS 108 may transmit the results to the healthcare provider office system 102. For example, without limitation, the LIS 108 may integrate the testing results into the EHR 104. In exemplary embodiments, the testing may comprise medication efficacy testing and the LIS 108 may be configured to flag ineffective medications as allergies at the patient file at the EHR 104.

The LIS 108 may be configured to determine, from the information obtained from the payor or prior authorization provider 110, any payment owed by the payor or prior authorization provider 110 and may be configured to be automatically generate an invoice with the owned amount and transmit the invoice the payor or prior authorization provider 110 with the reference number and other necessary information. The call center notices may comprise the reference number for tracking purposes. In exemplary embodiments, the invoice may be generated and transmitted electronically. In this may, payment may be secured by the laboratory without intervention by the healthcare provider office and/or the user. This may reduce the need for duplicate invoicing information which otherwise would be sent to the healthcare provider and then on to the payor, thereby reducing burdens on sever use and electronic storage.

The transmissions, receipts, parsing, generation, and the like shown and/or described herein may be accomplished electronically. This may reduce or eliminate the number of human interactions required. This may reduce the potential for error and/or speed up data processing. For example, without limitation, the system may be configured to achieve an error rate of less than 1%. This may reduce the need for certain healthcare provide resources, thereby reducing costs and complexity. The entire process may be completed while the specimen is in transit to the laboratory system 106, though such is not required. The specimen, upon arrival, may be associated with the reference number for tracking purposes. Such association may be made by way of a barcode, QR code, label, identifier, some combination thereof, or the like which may be physically associated with the specimen.

The LIS 108 may comprise data indicating prior authorization providers associated with various insurance providers such that the insurance provider may be contacted directly, or prior authorization provider may be contacted when appropriate. Such data may be stored at one or more remote databases.

The predetermined amount which triggers contacting the patient to collect payment may be specified in a consent document. The billing consent document may be provided to the healthcare provider office system 102. The billing consent document may be signed at the same time the specimen is collected, and may inform the patient that they may or may not receive a call in the next day or so. The consent document may be provided in electronic form and may be electronically returned to the LIS 108 for recordation. The consent document may be electronically generated by the LIS 108 and electronically transmitted to the healthcare provider office system 102, such as but not limited to by way of the EHR 104, for patient 116 signature though such is not required. In other exemplary embodiments, a paper or other copy of the consent document may be provided to the patient and may be scanned or otherwise converted to electronic form for storage. The consent document may form part of the proposed or suggested order, though such is not required.

While certain systems, such as but not limited to the call center system 112, the payment processing system 114, are illustrated as separate from the laboratory system 106, such systems may be integrated with the laboratory system 106 and may be provided as subsystems of the LIS 108, for example.

Figure 11:
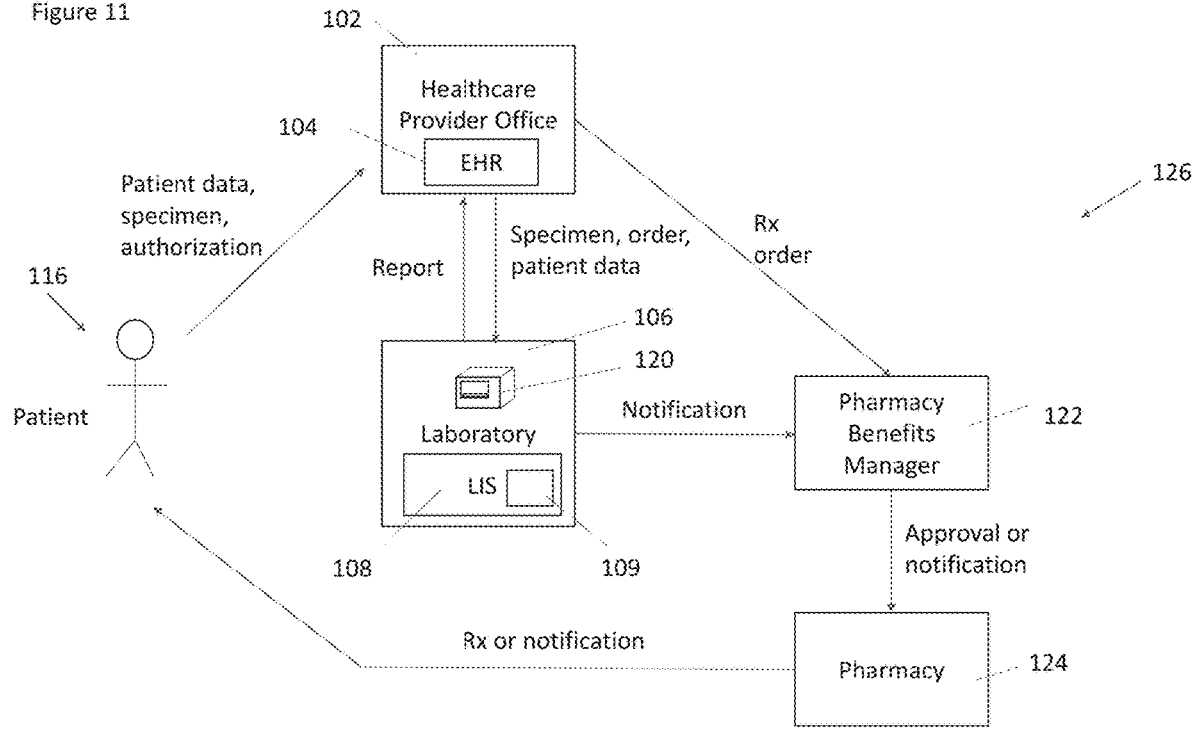
FIG. 11 is an exemplary pharmacy notification system in accordance with the present invention.
Figure 12:
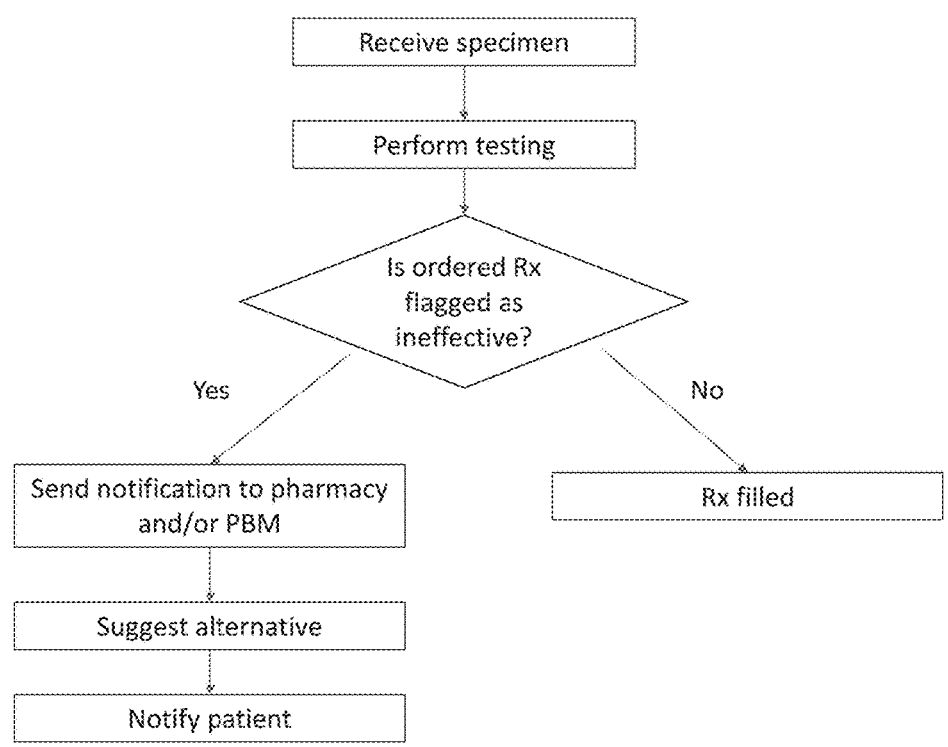
FIG. 12 is a flowchart with exemplary logic for operating the system of FIG. 11.

FIG. 11 is an exemplary pharmacy notification system 126 in accordance with the present invention and FIG. 12 is a flowchart with exemplary logic for operating the pharmacy notification system 126. Patent data may be received at the LIS 108 from the healthcare provider office 102. Such patient data may include prescribed and/or reported medications. Such patient data may be received from the patent 116 during an appointment and recorded at the EHR 104. The healthcare provider 102 may order certain genetic efficacy testing. Such orders may be recorded at the EHR 104. The patient 116 may also provide authorization for testing and/or give a specimen for testing at the appointment.

The specimen, ordered testing information, and patient data may be transmitted to the laboratory 106 as shown and described herein. Once the testing is completed, a report may be transmitted back to the healthcare provider office 102 and/or integrated into the EHR 104 as shown and described herein.

A notification regarding medications flagged as ineffective based on the ordered testing results may be sent to one or more pharmacy benefits providers ("PBM") 122. Such transmission may be alternatively to, or in addition to, transmission to the healthcare provider office 102 and/or direct integration with the EHR 104. The PBMs 122 may electronically or otherwise interface with dispensing pharmacies 124 for the patients 116. Interfacing with the PBMs 122 may provide an effective way to reach a large number of patients 116 as each PBM 122 may manage pharmacy benefits for a larger population of patients 116. While prescription orders may be sent directly to the PBM 122, in other exemplary embodiments, the prescriptions may first be sent to the filling pharmacy 124 who may relay them to the PBM 122.

The notification may indicate that one or more medications have been determined to be ineffective based on the patient's 116 genetic makeup. The healthcare provider office 102 and/or the pharmacy 124 may relay requests for coverage approval for certain medications. The PBM 122 may notify the pharmacy 124 that coverage is denied and/or to not fill one or more prescriptions where they are indicated as being ineffective in the testing results received from the LIS 108. In this way, the pharmacy 124 may be prevented from filling the prescription(s) and/or the patient 116 may be prevented from ever receiving the prescribed medication(s), thus reducing costs.

The notification may indicate that one or more medications have been determined to be effective based on the patient's 116 genetic makeup. The PBM 122 may notify the pharmacy 124 to proceed with filling one or more prescriptions which are indicated as effective in the testing results (e.g., those not indicated as being ineffective), thereby reducing costs by ensuring only effective medications are filled and dispensed. In other exemplary embodiments, a lack of notification after a period of time may be treated as an indication that such prescribed medications are considered effective. The notification may take the form of a claim denial and/or the PBM 122 may be configured to automatically generate a claim denial upon receipt of such a notification. Such requests for coverage may be transmitted with, or separately from, the testing results. Such requests may be transmitted around the same time as the testing, or much later.

The notifications described herein may be electronic in nature and may be electronically transmitted between computerized systems located at the laboratory 106, the PBM 122, and/or the pharmacy 124. Alternatively, or additionally, such notification may be made by phone, email, text message, automated call, some combination thereof, or the like.

Where one or more prescriptions are indicated as being ineffective, the LIS 108 may be configured to provide alternative medications, in the notification or separately, which are effective based on the patient's genetic makeup. In such cases, the PBM 122 may notify the pharmacy 124 of such alternatives which may be presented to the patient 116 for approval and/or substituted automatically. The notification may flag the ineffective medications as an allergy in the patient's 116 file at the PBM 122 system and/or the pharmacy 124 system. This may permit integration into existing systems such as but not limited to those which utilize and/or interface with EHRs 104. This may, alternatively or additionally, provide automatic notification in the event of future attempts to prescribe and/or dispense such flagged medications and/or treatments. The notification may comprise the full report transmitted to the healthcare provider's office 102, such as for integration into the EHR 104, or may be a different (e.g., simplified, reformatted) version. In other exemplary embodiments, the notification may be sent directly the pharmacy 124.

Any of the embodiments shown and described herein may be used together or separately from one another. For example, without limitation, the laboratory based prior authorization system 100 may be used separately from, on in conjunction with, the pharmacy notification system 126. As yet another example, the interface 60 may be provided at the LIS 108, the EHR 104, the PBM 122, the pharmacy 124, some combination thereof, or the like.

Figure 13:
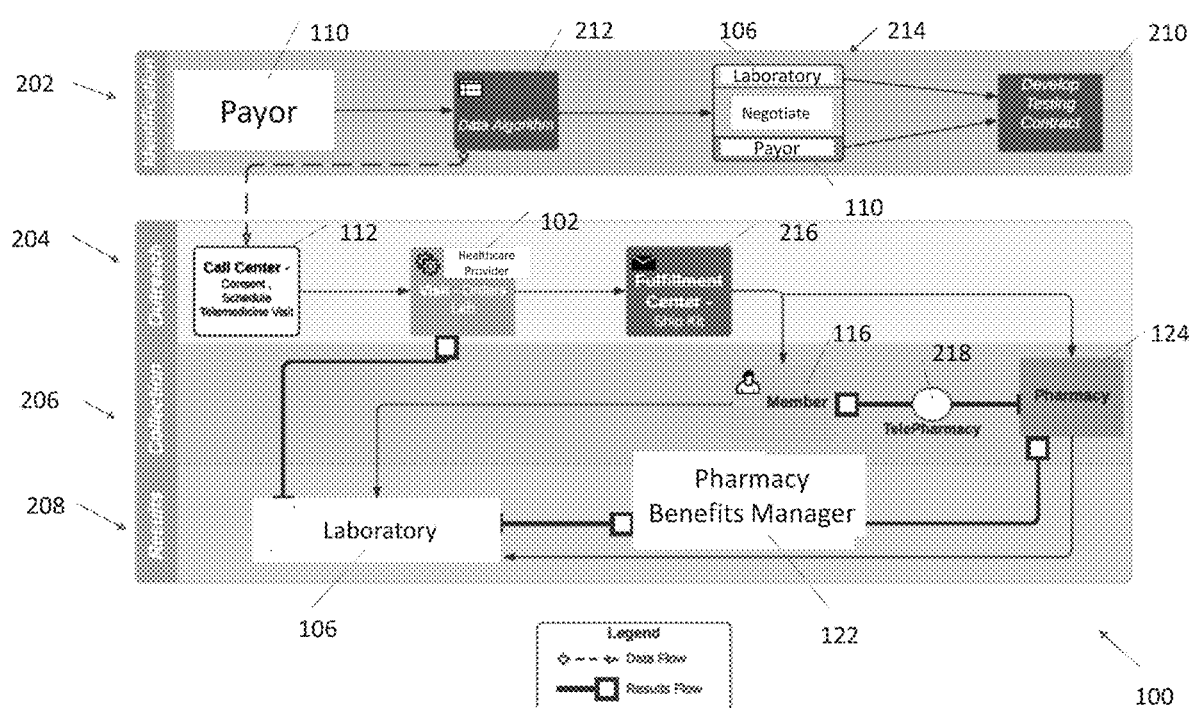
FIG. 13 is another exemplary pharmacy notification system and flow chart in accordance with the present invention.

FIG. 13 illustrates another exemplary system 100 and flow chart for operating the same in accordance with the present invention. As part of an identification process 202, the payor 110 may work with the laboratory 106 to develop a testing contract 210. The testing contract 210 may be developed, at least in part, by the payor 110 executing a data algorithm or filter 212 which identifies members 116 of its population which are likely eligible for testing. The data algorithm or filter 212 may be configured to identify members 116 having known diseases or conditions and/or reported to be taking medications or undergoing treatments which may render the member 116 eligible for testing. Such diseases or conditions and/or medications or treatments may be identified by way of standardized coding, such as but not limited to IDC 10 codes. E.g., F32.9 Depression ICD10. In this way, the payor 110 and/or the laboratory 106 may identify the extent of testing likely to be needed. The laboratory 106 and payor 110 may negotiate 214 and enter an agreement 210. The agreement 210 may comprise a flat fee, a per test fee, a subscription model, monthly payments, annual payments, some combination thereof, or the like. For example, without limitation, With the agreement 210 established, an outreach phase 204 may begin. The call center 112 may reach out to each patient 116 identified by the data algorithm or filter 212. Outreach efforts may include telephonic calls, video calls, automated calls, emails, text messages, letter campaigns, some combination thereof, or the like. The outreach efforts may identify the payor 110 covered testing available to the patient 116. Such outreach efforts may, alternatively or additionally, be made to healthcare providers 102. The call center 112 representative may establish contact, inform the patient 116 of the eligible testing, request and receive consent for testing, and schedule a visit with a healthcare provider 102 who orders the testing, such as but not limited to, genetic efficacy testing. Such outreach efforts may be undertaken by the automated generating and transmission of instructions for the same.

The healthcare provider 102 may be the same or a different from the patient's 116 normal healthcare providers 102. In exemplary embodiments, the healthcare provider 102 may provide a telemedicine consultation and one or more orders for the lab panel. The orders may be electronically transmitted to the laboratory 106.

Upon ordering, the healthcare provider 102 may electronically transmit the order to a fulfillment center 216. The fulfillment center 216 may ship a kit directly to the patient 116 and/or their pharmacy 124 for gathering the genetic material for testing. The kit may include, for example without limitation, the genetic material gathering device 10, instructions for collection, a consent form, an invoice, return instructions, return label, some combination thereof, or the like.

During a collection phase 206, the patient 116 and/or their pharmacy 124 may collect the genetic material, such as but not limited to, by way of the genetic material gathering device 10 provided in the kit from the fulfillment center 216. The kit and/or the genetic material gathering device 10 may be delivered to the laboratory 106. For example, without limitation, such collection may be done by a self-swab, a drive through swab, or a face-to-face encounter.

The laboratory 106 may perform the ordered testing. The results may be transmitted to the PBM 122. The PBM 122 may integrate the results by flagging any ineffective or undereffective medications and/or treatments as an allergy in the patient file. This may prevent future approval of such medications and/or treatments, and/or may permit integration with existing systems. The PBM 122 may deny coverage for such ineffective or undereffective medications and/or treatments. Results may also be transmitted to one or more of the healthcare providers 102 and the pharmacy 124.

The PBM 122 may contact the pharmacy 124 regarding approved or denied prescription medication coverage based on the testing results. Such contact may be made by way of electronic notification. The pharmacy 124 may contact the patient 116 regarding such results and/or coverage approvals or denials. Such contact may be made by way of electronic notification. The testing results may include possible alternative medications and/or treatments which may likewise by relayed to the patient 116.

The pharmacy 124 may utilize a tele-pharmacy system 218 to contact the patient 216 regarding testing, results, coverage approval/denial, alternative medications or treatments, some combination thereof, or the like.

Any embodiment of the present invention may include any of the optional or preferred features of the other embodiments of the present invention. The exemplary embodiments herein disclosed are not intended to be exhaustive or to unnecessarily limit the scope of the invention. The exemplary embodiments were chosen and described in order to explain the principles of the present invention so that others skilled in the art may practice the invention. Having shown and described exemplary embodiments of the present invention, those skilled in the art will realize that many variations and modifications may be made to the described invention. Many of those variations and modifications will provide the same result and fall within the spirit of the claimed invention. It is the intention, therefore, to limit the invention only as indicated by the scope of the claims.

Certain operations described herein may be performed by one or more electronic devices. Each electronic device may comprise one or more processors, electronic storage devices, executable software instructions, and the like configured to perform the operations described herein. The electronic devices may be general purpose computers of specialized computing device. The electronic devices may be personal computers, smartphone, tablets, databases, servers, or the like. The electronic connections described herein may be accomplished by wired or wireless means. The computerized hardware, software, components, systems, steps, methods, and/or processes described herein may serve to improve the speed of the computerized hardware, software, systems, steps, methods, and/or processes described herein.

What is claimed is:

1. A system for preventing the coverage or fill of ineffective medications through integration of genetic efficacy testing results with a legacy electronic health record ("EHR") system, said system comprising:
    the legacy EHR system associated with a healthcare provider, wherein said legacy EHR comprises patient data for a patient;
    an efficacy database comprising data regarding medications known to have reduced or no efficacy in persons having particular genetic markers;
    one or more genetic sequencing machines associated with a laboratory;
    a laboratory information system ("LIS") associated with the laboratory and in electronic communication with the legacy EHR system and the one or more genetic sequencing machines, wherein said LIS comprises software instructions stored at one or more electronic storage devices, which when executed, configures one or more processors to:
        receive a request for genetic efficacy testing for the patient from the legacy EHR;
        electronically command performance of the genetic efficacy testing for the patient at the one or more genetic sequencing machines;
        receive genetic efficacy testing results comprising genetic markers for the patient from the one or more genetic sequencing machines; and
        query the efficacy database to identify any medications known to have reduced or no efficacy in persons having the same genetic markers as the patient;
    a pharmacy system associated with a dispensing pharmacy for the patient;
    a pharmacy benefits manager ("PBM") system associated with a PBM and in electronic communication with the LIS, and the pharmacy system, wherein said PBM system comprises software instructions stored at one or more electronic storage devices, which when executed, configures one or more processors to:
        receive said genetic efficacy testing results from the LIS;
        electronically flag any medications identified as ineffective or undereffective in the received testing results in an existing field of an electronic file associated with the patient at the legacy EHR system, wherein the existing field is designated for use other than storage of genetic efficacy test result data;
        receive a coverage request for a prescription medication for the patient; and
        if the ordered prescription medication is contraindicated in the electronic file associated with the patient at the legacy EHR system, generate and transmit an electronic notification to the pharmacy system requesting that the ordered prescription medication not be filled.

2. The system of claim 1 wherein:
    additional software instructions stored at the one or more electronic storage devices of the PBM, which when executed, configures the one or more processors of the PBM to automatically transmit a claim denial for any medications contraindicated at the existing field in the electronic file associated with the patient.

3. The system of claim 1 further comprising:
    an alternative medication database comprising a list of alternative treatment options, each of which is associated with one or more medications; and
    additional software instructions stored at the one or more electronic storage devices of the LIS, which when executed, configure the one or more processors of the LIS to:
        query the alternative medication database to retrieve alternative treatment options associated with medications matching the medications identified as being ineffective or undereffective for the patient in the testing results; and
        include each of the retrieved alternative medications in the testing results; and
    additional software instructions stored at the one or more electronic storage devices of the PBM, which when executed, configures the one or more processors of the PBM to include a request to substitute any ordered prescription medications contraindicated at the existing field in the electronic file associated with the patient with the retrieved alternative medication associated with the flagged medication.

4. The system of claim 1 further comprising:
one or more genetic sequencing machines associated with the laboratory and in electronic communication with the LIS; and
additional software instructions stored at the one or more electronic storage devices of the LIS, which when executed, configure the one or more processors of the LIS to, automatically and electronically command performance of the genetic efficacy testing, at the one or more genetic sequencing machines, wherein the genetic testing results are electronically received from the one or more genetic sequencing machines.

5. The system of claim 1 further comprising:
additional software instructions stored at the one or more electronic storage devices of the LIS, which when executed, configures the one or more processors of the LIS to transmit the genetic efficacy testing results to the legacy EHR system, wherein said legacy EHR system is configured to electronically contraindicate any medications identified as ineffective or undereffective in the received testing results at the existing field in the patient data forming the electronic file for the patient.

6. The system of claim 5 wherein:
said legacy EHR system is configured to generate an alert upon changes to patient data at the legacy EHR system indicating proposed prescription of any medication contraindicated at the legacy EHR system in association with the patient.

7. The system of claim 1 further comprising:
a payor database comprising a number of insured members of an insurance population, including said patient; and
a filtering system configured to identify subsets of said members of said insurance population identified as having one or more diseases indicating eligibility for genetic efficacy testing.

8. The system of claim 7 further comprising:
a call center in electronic communication with said filtering system and configured to receive data regarding identified subsets of said members and automatically and electronically initiate a contact campaign informing said members of said subset of eligibility for testing; and
a fulfillment center in electronic communication with the legacy EHR system and configured to electronically receive said request for genetic efficacy testing and automatically generate a shipping label for shipment of a testing kit comprising a genetic material gathering device for said patient, instructions for performing genetic testing, and a pre-paid return label for said laboratory.

9. The system of claim 1 further comprising:
a telemedicine subsystem associated with said healthcare provider and configured to facilitate telemedicine appointments with said patient; and
a tele-pharmacy subsystem associated with the pharmacy and configured to facilitate tele-pharmaceutical communications with said patient.

10. A method for preventing the coverage or fill of ineffective medications through integration of genetic efficacy testing results with legacy electronic files, said method comprising the steps of:

receiving patient data at a laboratory information system ("LIS") associated with a laboratory from a legacy electronic health record ("EHR") system associated with a healthcare provider, wherein said patient data comprises an order for genetic efficacy testing for a patient;
generating, at the LIS electronic instructions to perform tests in accordance with the order at a genetic sequencing machine;
receiving, at the LIS, genetic testing results comprising genetic markers for the patient performed by the genetic sequencing machine;
querying, by way of the LIS, an efficacy database comprising data regarding medications known to have reduced or no efficacy in persons having particular genetic markers with each of the genetic markers received at the LIS from the genetic sequencing machine;
determining at the LIS that at least one medication is ineffective for the patient based on the patient's genetic makeup;
generating an electronic notification at the LIS comprising the at least one ineffective medication;
transmitting the electronic notification to a legacy pharmacy benefits manager ("PBM") system in electronic communication with said LIS;
electronically contraindicating the at least one ineffective medication in the electronic notification at an existing field in the legacy electronic file associated with the patient at the PBM system, wherein the existing field is designated for use other than storage of genetic efficacy test result data;
receiving at the PBM system an electronic request for coverage of the at least one ineffective medication from a dispensing pharmacy system; and
sending, from the PBM system to the dispensing pharmacy system, a denial of coverage notice for the at least one ineffective medication.

11. The method of claim 10 further comprising the steps of:
identifying, from a database of covered members of an insurance population, a subset of members eligible for genetic efficacy testing using an electronic filtering algorithm configured to identifying members associated with certain standardized disease or treatment codes;
transmitting electronic instructions to a call center to contact each member of said subset for consent to perform genetic efficacy testing; and
electronically scheduling an appointment with the healthcare provider for each consenting member of said subset.

12. The method of claim 11 further comprising the steps of:
transmitting electronic instructions from the healthcare provider to a fulfilment center for shipment of genetical material gathering kits to each patient for whom genetic efficacy testing is ordered, wherein said genetic material gathering kits comprise a genetic material gathering device, instructions for gathering genetic material, and a pre-paid label for return shipment to the laboratory.

13. The method of claim 10 further comprising the steps of:
querying an alternative medication database in electronic communication with the LIS and comprising a list of alternative treatments, each of which is associated with one or more medications, with each of the at least one ineffective medication to retrieve alternative treatment options for each of the at least one ineffective medication; and sending, from the legacy PBM system to the dispensing pharmacy system, approval to substitute the at least one ineffective medication with the retrieved alternative medication.

14. The method of claim 10 further comprising the steps of:

receiving, from the legacy EHR one system, one or more current medications for said patient;

comparing, at the LIS, the medications received from the efficacy database with the current medications; and transmitting a report to the legacy EHR system indicating all of the current medications known to have reduced or no efficacy in persons having the same genetic markers as the patient.

15. The method of claim 10 further comprising the steps of:

transmitting the electronic notification to the legacy EHR system; and contraindicating the at least one ineffective medication in the electronic notification by electronically flagging the at least one ineffective medication as an allergy at the existing field of the legacy electronic file associated with the patient at the legacy EHR system.

16. The method of claim 15 further comprising the steps of:

receiving at the legacy EHR system a prescription for a new medication;

determining, at the legacy EHR system, that the new medication is flagged contraindicated at the existing field of in the electronic file associated with the patient; and generating, at the legacy EHR system, a notification indicating that the new medication is contraindicated.

17. The method of claim 10 further comprising the steps of:

receiving at the legacy PBM system an electronic request for coverage of a second medication from the dispensing pharmacy system;

determining at the legacy PBM system that the second medication is not contraindicated at the existing field in the electronic file associated with the patient at the legacy PBM system; and sending, from the legacy PBM system to the dispensing pharmacy system, a coverage approval for the second medication.

18. A system for preventing the coverage or fill of ineffective prescribed medications through integration of genetic efficacy testing results with a legacy electronic patient file, said the system comprising:

a payor database comprising a listing of covered members of an insurance population, wherein each of said covered members is associated with at least one standardized disease code and at least one standardized treatment code;

a filtering subsystem configured to generate a subset of said covered members associated with particular standardized disease codes or standardized treatment codes;

a call center configured to receive said subset of covered members and electronically contact each of said members in said subset for consent to perform genetic efficacy testing and schedule telemedicine appointments for consenting members of said subset;

a legacy electronic health record ("EHR") system associated with a telemedicine provider;

a laboratory information system ("LIS") associated with a laboratory and in electronic communication with the legacy EHR system;

a dispensing pharmacy system;

a legacy pharmacy benefits manager ("PBM") system associated with a PBM and in electronic communication with the LIS and the dispensing pharmacy system;

an alternative medication database in electronic communication with the LIS and comprising a list of alternative treatment options, each of which is associated with one or more medications;

an efficacy database in electronic communications with the LIS and comprising data regarding medications known to have reduced or no efficacy in persons having particular genetic markers;

a genetic sequencing machine in electronic communication with the LIS; and software instructions stored at one or more electronic storage devices of the LIS, which when executed, configure one or more processors of the LIS to:

receive orders for genetic efficacy testing from said legacy EHR system;

generate instructions to perform the ordered tests;

transmit said instructions to the genetic sequencing machine;

receive genetic testing results comprising genetic markers for the patient from the genetic sequencing machine;

query the efficacy database to determine prescribed medications known to have reduced or no efficacy in persons having the same genetic markers as the patient ("ineffective medications");

query the alternative medication database to retrieve alternative treatment options associated with medications matching the ineffective medications; and transmit a report to the legacy EHR system and the legacy PBM system comprising the ineffective medications and the retrieved alternative treatment options;

software instructions stored at one or more electronic storage devices of the legacy PBM system, which when executed, configure one or more processors of the legacy PBM system to:

flag the ineffective medications in the report as an allergy in a legacy allergy field of the legacy electronic patient file associated with said patient;

receive coverage requests for certain medications; and issue claim denials to said dispensing pharmacy system for said certain medications where said certain medications match those flagged as an allergy at the legacy allergy field of the legacy electronic patient file for the patient; and software instructions stored at one or more electronic storage devices of the WE-R legacy EHR system, which when executed, configure one or more processors of the legacy EHR system to:

flag the ineffective medications in the report as an allergy in the legacy allergy field of the legacy electronic file associated with said patient;

receive prescriptions for medications; and generate an electronic notification for said prescribed medications where said prescribed medications match those flagged as an allergy in the legacy electronic file for the patient.

19. The system of claim 1 wherein:
the existing field comprises a legacy allergy field; and
contraindication is provided by flagging the medications known to have reduced or no efficacy in persons having the same genetic markers as the patient as an allergy at the legacy allergy field.

20. The method of claim 10 wherein:
the existing field comprises a legacy allergy field; and
contraindication is provided by flagging the medications known to have reduced or no efficacy in persons having the same genetic markers as the patient as an allergy at the legacy allergy field.

\* \* \* \* \*

UNITED STATES PATENT AND TRADEMARK OFFICE
CERTIFICATE OF CORRECTION

PATENT NO. : 11,398,312 B2
APPLICATION NO. : 16/945198
DATED : July 26, 2022
INVENTOR(S) : Rob Todd et al.

It is certified that error appears in the above-identified patent and that said Letters Patent is hereby corrected as shown below:

In the Claims

Column 29, Claim 14, Line 10, please delete the word "one" before the word system.
Column 30, Claim 18, Line 57, please delete "WE-R".

Signed and Sealed this
Twenty-seventh Day of September, 2022

Katherine Kelly Vidal
*Director of the United States Patent and Trademark Office*